US009039667B1

(12) United States Patent
Hen et al.

(10) Patent No.: US 9,039,667 B1
(45) Date of Patent: *May 26, 2015

(54) HEMOSTATIC DEVICE AND METHOD

(71) Applicant: Biolife, L.L.C., Sarasota, FL (US)

(72) Inventors: John Hen, Bradenton, FL (US); Talmadge Kelly Keene, Wimauma, FL (US); Mark Travi, Venice, FL (US)

(73) Assignee: Biolife, L.L.C., Sarasota, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/606,324

(22) Filed: Jan. 27, 2015

Related U.S. Application Data

(63) Continuation of application No. 13/847,057, filed on Mar. 19, 2013, now Pat. No. 8,961,479.

(51) Int. Cl.
A61M 35/00 (2006.01)
A61L 15/18 (2006.01)
(Continued)

(52) U.S. Cl.
CPC ............ *A61L 15/18* (2013.01); *A61L 2400/04* (2013.01); *A61L 2300/418* (2013.01); *A61L 2300/102* (2013.01); *A61B 17/0057* (2013.01); *A61F 2013/00412* (2013.01); *A61M 35/003* (2013.01); *A61F 13/36* (2013.01); *A61M 35/00* (2013.01); *A61F 13/00* (2013.01)

(58) Field of Classification Search
CPC .... A61M 35/00; A61M 35/003; A61L 15/18; A61L 2400/04; A61L 2300/418; A61L 2300/102; A61B 17/0057; A61F 13/36; A61F 2013/00412; A61F 13/00

USPC .................................. 604/290, 299; 606/214
See application file for complete search history.

(56) References Cited

U.S. PATENT DOCUMENTS 2,923,664 A 2/1960 Cook et al.
3,368,911 A 2/1968 Kuntz et al.
(Continued)

FOREIGN PATENT DOCUMENTS

EP 1632252 A1 3/2006
EP 1 276 463 B1 12/2010
(Continued)

OTHER PUBLICATIONS

Kuo et al. (J. Vasc. Interv. Radiol. 19:1 72-79 2008).
(Continued)

*Primary Examiner* — Tatyana Zalukaeva
*Assistant Examiner* — Andrew J Mensh
(74) *Attorney, Agent, or Firm* — Charles J. Prescott

(57) ABSTRACT

A method of arresting blood flow from a bleeding wound including the steps of (1) providing a solid hemostatic tablet preferably including potassium ferrate and a cation ion exchange resin pressure formed into a tablet for delivery onto a bleeding wound, the tablet defining a proximal portion and a distal portion, (2) applying the proximal portion against the bleeding wound to improve the rate of adhesion to a bleeding wound surface, and then (3) applying pressure against the tablet over the wound site. After the seal is formed from the interaction of blood or exudates with the proximal portion of the tablet, the distal portion of the tablet delaminates from the proximal portion to form a reservoir to stop further bleeding and to provide antimicrobial protection and healing. The tablet may be applied to any surface orientation and take any shape and thickness possible.

20 Claims, 18 Drawing Sheets

(51) Int. Cl.
*A61D 1/00* (2006.01)
*A61B 17/00* (2006.01)
*A61F 13/00* (2006.01)
*A61F 13/36* (2006.01)

(56) References Cited

U.S. PATENT DOCUMENTS

| | | | |
|---|---|---|---|
| 4,292,972 | A | 10/1981 | Pawelchak et al. |
| 4,545,974 | A | 10/1985 | Thompson |
| 4,551,326 | A | 11/1985 | Thompson |
| 4,606,843 | A | 8/1986 | Kaczur |
| 4,851,230 | A | 7/1989 | Tencza et al. |
| 5,269,803 | A | 12/1993 | Geary et al. |
| 6,187,347 | B1 | 2/2001 | Patterson et al. |
| 6,228,930 | B1 | 5/2001 | Dairoku et al. |
| 6,521,265 | B1 | 2/2003 | Patterson |
| 6,890,344 | B2 | 5/2005 | Levinson |
| 8,119,160 | B2 | 2/2012 | Looney et al. |
| 8,269,058 | B2 | 9/2012 | McCarthy et al. |
| 2009/0252799 | A1* | 10/2009 | Hen et al. ............... 424/486 |
| 2010/0129427 | A1 | 5/2010 | Hen et al. |
| 2011/0245868 | A1 | 10/2011 | Teeslink et al. |

FOREIGN PATENT DOCUMENTS

| | | |
|---|---|---|
| WO | 2004/041313 A2 | 5/2004 |
| WO | 2012/007929 A1 | 1/2012 |

OTHER PUBLICATIONS

Michelson (The American Journal of Cosmetic Surgery 25-3 2008).
The Merck Manual of Medical Information Home Edition (1997). (Sec. 2, Ch. 6, p. 29), Rahway, NJ: Merck & Co., Inc.
Narins, Craig R. et al., A Prospective, Randomized Trial of Topical Hemostasis Patch Use following Percutaneous Coronary and Peripheral Intervention, J Invasive Cardiol 2008; 20:579-584.
Younger, Alistair S.E. et al., Wide Contoured Thigh Cuffs and Automated Limb Occlusion Measurement Allow Lower Tourniquet Pressures, Clinical Orthopaedics and Related Research, No. 428, pp. 286-293, (2004) Lippincott Williams & Wilkins.
Wang, Xu et al. Comparison of a Novel Hemostatic Agent to Currently Available Agents in a Swine Model of Lethal Arterial Extremity Hemorrhage, University of Michigan, Department of Emergency Medicine, Ann Arbor, MI.

* cited by examiner

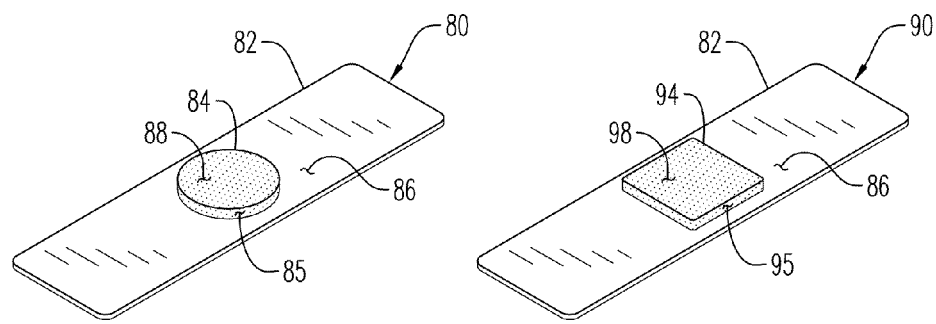
FIG. 25   FIG. 26
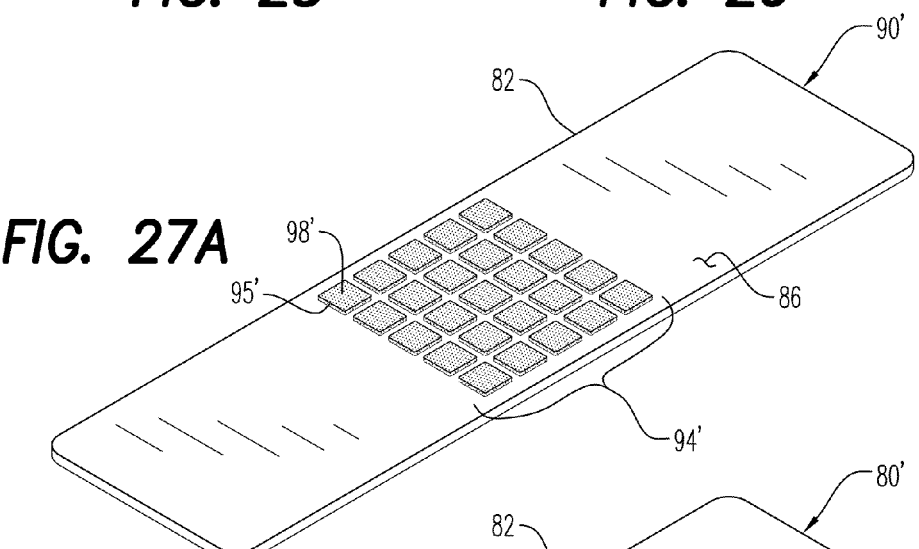
FIG. 27A
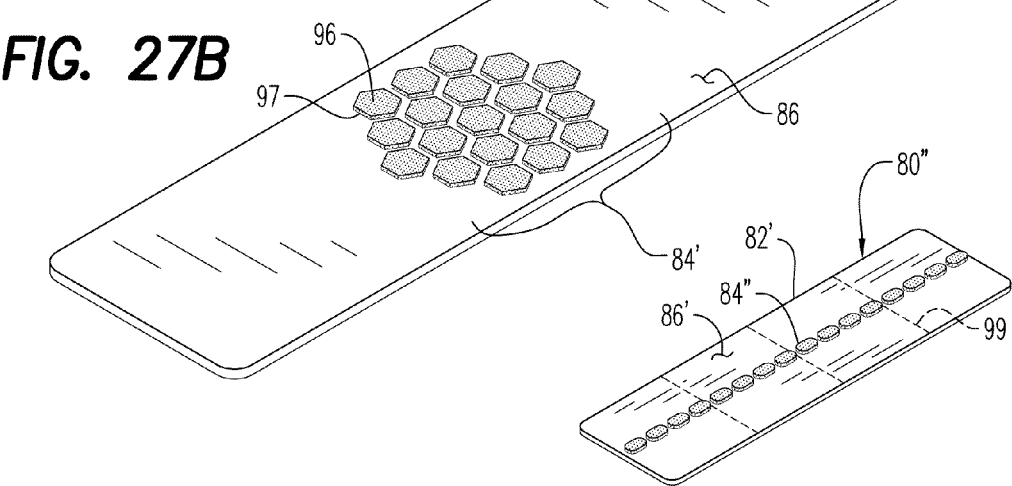
FIG. 27B
FIG. 27C

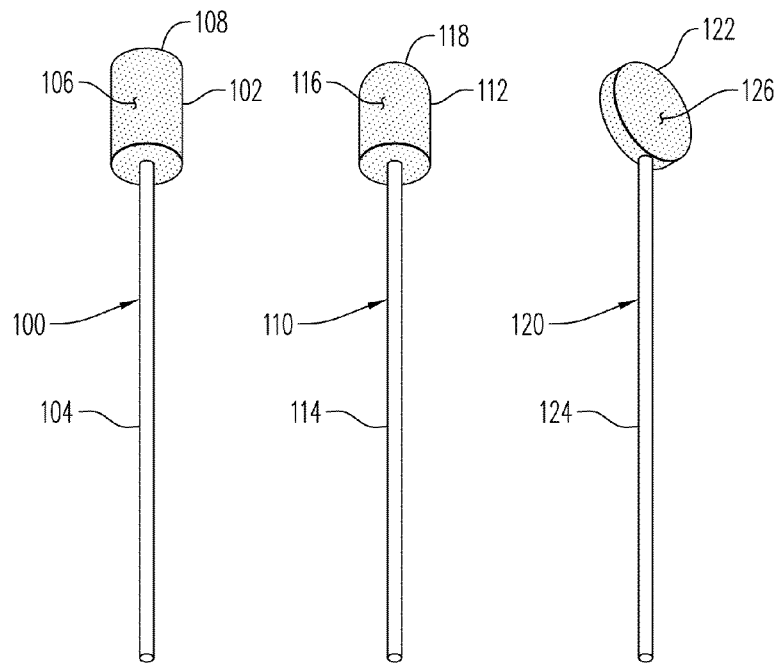
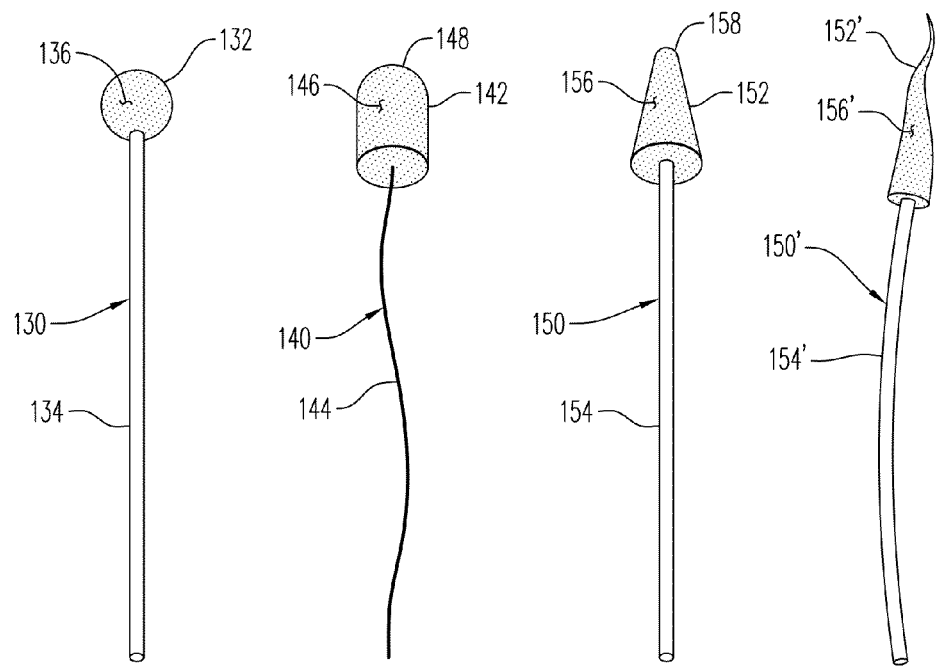
FIG. 28  FIG. 29  FIG. 30
FIG. 31  FIG. 32  FIG. 33  FIG. 33A

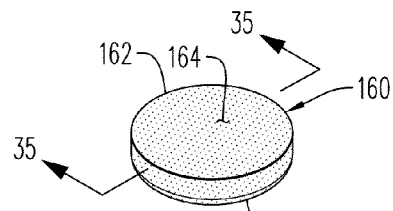
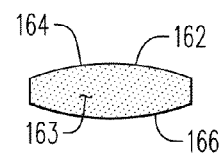
FIG. 34   FIG. 35
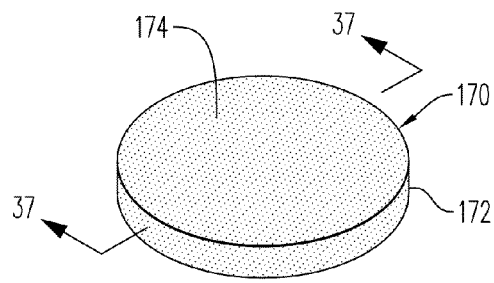
FIG. 36
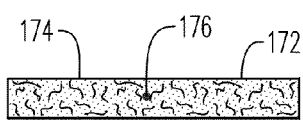
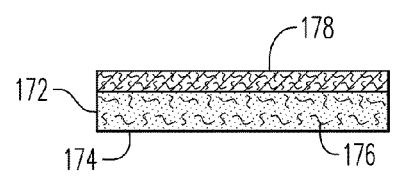
FIG. 37
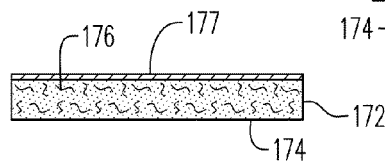
FIG. 37B
FIG. 37A
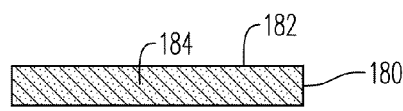
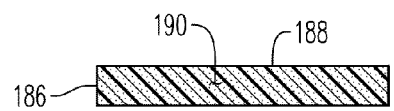
FIG. 37C   FIG. 37D
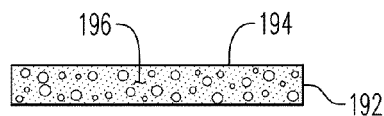
FIG. 37E

| #1 | #2 | #3 |
|---|---|---|
| PERCENTAGE WHOLE BEADS 0 TO 60% PERCENTAGE FRAGMENTS 40 TO 100% | PERCENTAGE WHOLE BEADS 61 TO 89% PERCENTAGE FRAGMENTS 39 TO 11% | PERCENTAGE WHOLE BEADS 90 TO 100% PERCENTAGE FRAGMENTS 0 TO 10% |
| THESE RATIOS FORM COMPLETE TABLETS WITH GOOD INTEGRITY. | THESE RATIOS FORM TABLETS, BUT DUE TO SETTLING AND SEPARATION OF THE PARTICLES IN THE DIE, THERE ARE NOT SUFFICIENT FRAGMENTS TO FORM A STRONG COMPLETE TABLET. THE EXPOSED WHOLE BEADS EASILY FALL FROM THE TABLET | THESE RATIOS ARE NOT SUFFICIENT TO FORM A TABLET. AFTER COMPRESSING THE SPHERES SIMPLY FALL APART. |
| 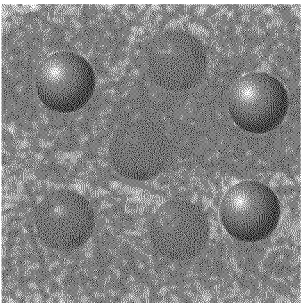 | 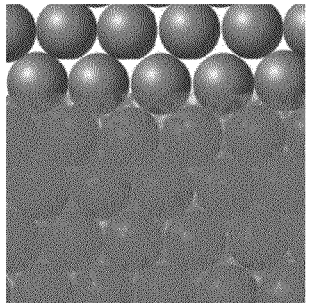 | 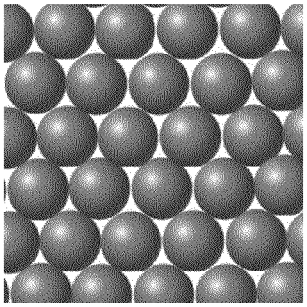 |
| THIS PHOTO IS OF TWO 1/2 TABLETS WITH GOOD INTEGRITY. | COMPLETE EXPOSED WHOLE BEADS ARE NO LONGER ADHERED FIRMLY TO TABLET. | COMPRESSED WHOLE BEADS WILL NOT HOLD SHAPE ONCE REMOVED FROM THE TABLET DIE. |
| 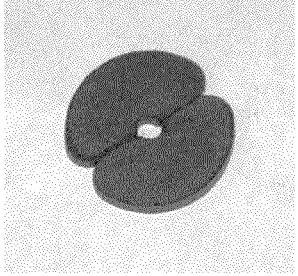 | 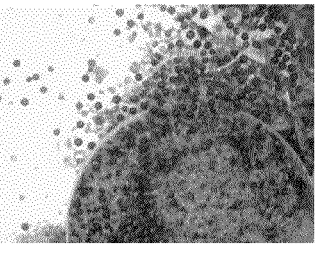 | 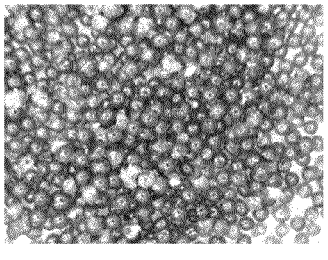 |

FIG. 46

THICKNESS STUDY: THESE TABLETS WERE 20mm IN DIAMETER
| | MASS OF POWDER | PSI | THICKNESS (mm) | PHOTO |
|---|---|---|---|---|
| 1 | 0.1087 GRAMS OF BIOLIFE POWDER<br><br>DESCRIPTION: FALLS APART | 29k | 0.426 |  |
| 2 | 0.2028 GRAMS OF BIOLIFE POWDER<br><br>DESCRIPTION: TABLET FORMED BUT FRAGILE AND UNSTABLE | 29k | 0.535 | 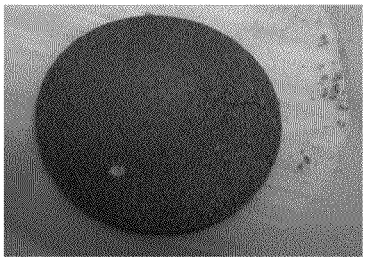 |
| 3 | 0.2031 GRAMS OF BIOLIFE POWDER<br><br>DESCRIPTION: TABLET FORMED SURPRISING STRENGTH | 45k | 0.531 | 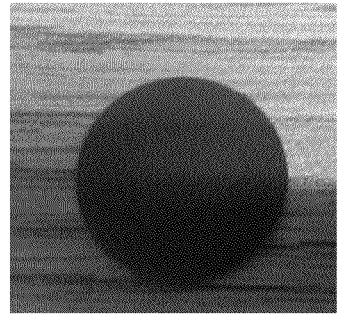 |
FIG. 47

HEMOSTATIC DEVICE AND METHOD

CROSS-REFERENCE TO RELATED APPLICATIONS

This application is a continuation of application Ser. No. 13/847,057, filed Mar. 19, 2013.

STATEMENT REGARDING FEDERALLY SPONSORED RESEARCH OR DEVELOPMENT

Not applicable

INCORPORATION-BY-REFERENCE OF MATERIAL SUBMITTED ON A COMPACT DISC

Not applicable

BACKGROUND OF THE INVENTION

1. Field of the Invention

This invention relates generally to hemostatic products, and particularly to the surprisingly improved performance of a novel hemostatic device which includes potassium ferrate and a cationic exchange resin when applied to a bleeding or exudating wound.

2. Description of Related Art

Hemostasis powders are well known. Thompson et al, U.S. Pat. Nos. 4,545,974 & 4,551,326, disclose processes for the manufacture of potassium ferrate and similar high oxidation state oxyiron compounds. Patterson et al U.S. Pat. No. 6,187,347 and Patterson et al. U.S. Pat. No. 6,521,265, disclose the mixing of potassium ferrate and anhydrous strongly acidic cation exchange resins for the cessation of bleeding. These patents are incorporated by reference herein in their entirety. Kuo et al. (J. Vasc Interv. Radial. 19:1 7279 2008) disclose the benefit of ferrate/resin mixtures in reducing the time to hemostasis (TTH) from 6 minutes to 4 minutes versus D-stat, the market leader in hemostasis pads. Michelson (The American Journal of Cosmetic Surgery 25-3 2008) shows that the ferrate/resin mixtures are excellent for wound care. Michelson demonstrated complete closure of a patient with twin brachial dehisced wounds following cosmetic surgery. After 16 weeks, the patient healed without scarring.

Cook et al. in U.S. Pat. No. 2,923,664 disclose a hemostatic tablet formed by the wet granulation and compression of a mixture of cellulose glycolic acid ether and its sodium salt. Kuntz et al. in U.S. Pat. No. 3,368,911 disclose a hemostatic sponge prepared by freeze drying acid swollen collagen fibrils. Pawelchak et al. in U.S. Pat. No. 4,292,972 disclose a lyophilized hydrocolloid foam possessing hemostatic properties. The prior art illustrates the hemostatic tablet or sponge but provide little comparison with the powder or granulation from which the tablet originates from.

There is an unmet need for providing an alternate means for delivering a hemostatic dressing onto a wound which avoids the mess associated with the handling, application and delivery of a loose, granular powder to the wound site. A solid device, preferably a tablet, formed from loose hemostatic powder is very dense due to the high compressive force to prepare the tablet. A loose powder compressed into a solid intuitively creates a less messy product application, but the compression process results in a reduction in surface area. Therefore, the free loose hemostatic powder would be expected to be faster acting compared to the solid tablet form of this material. The foregoing examples of the related art and limitations related therewith are intended to be illustrative and not exclusive. Other limitations of the related art will become apparent to those skilled in the art upon a reading of the specification and a study of the drawings.

BRIEF SUMMARY OF THE INVENTION

This invention is directed to a novel hemostatic device (to be marketed by Biolife, L.L.C. under the trademark STATSEAL) and method of arresting the flow of blood from a bleeding wound which is prepared from a powder or powderous mixture that preferably includes an effective amount of an insoluble cation exchange material preferably combined with an anhydrous salt ferrate compound. In the method, the device as a solid tablet is applied to the wound by pressing the tablet against the wound for a time sufficient to clot the blood to arrest substantial further blood flow from the wound.

Agglomerates

Size enlargement or agglomeration is any process whereby small particles are gathered into larger, relatively permanent masses in which the original particles can still be identified. Applications include formation of useful shapes (e.g., brick and tile) and irregular pellets or balls for the industrial beneficiation of finely divided materials.

Numerous benefits result from size-enlargement processes and, a wide variety of size-enlargement methods and applications are available, one of which is pressure compaction. Equipment used in pressure compaction includes piston or molding presses, tableting presses, roll-type presses, pellet mills, and screw extruders which provide for a wide variety of size-enlargement methods and applications. Agglomerate bonding mechanisms may be divided into five major groups: (1) solid bridges; (2) mobile liquid binding; (3) immobile liquid bridges; (4) intermolecular and electrostatic forces; (5) and mechanical interlocking. Robert H. Perry, ed. et al., (*Perry's Chemical Engineers' Handbook*, $6^{th}$ ed., 8-60-8-61 1984).

The STATSEAL hemostatic device of this disclosure prepared by pressure compaction, preferably from a powderous mixture of a potassium ferrate/strong acid cation exchange resin, provides improved delivery and control of the application onto the wound site without the messiness associated with loose powder application. The dense packing in, for example, a tablet in a topical application on a bleeding wound is expected to be slower acting compared to the free powder form of the same mixture in terms of the control of bleeding due to the reduction in surface area. Surprisingly, the opposite was found to be true; the hemostatic tablet adhered more tenaciously to the bleeding wound than the powder and stopped bleeding faster. Once a seal is formed, the bulk of the unused tablet easily delaminates from the seal, or the unused portion of the tablet left in place provides a reservoir of hemostatic dressing for sustained and longer term capacity to stop further bleeding and to provide antimicrobial protection and healing.

The solid hemostatic tablet can either be applied to a wound that is actively bleeding or to a site that may experience bleeding later. The solid hemostat may be used to also seal a site that is oozing exudative bodily fluids and create a seal in combination with blood or exudative fluids to keep the wound site dry, preventing maceration, while simultaneously preventing wound desiccation.

Mechanism of Action

1. The preferred 1:7 ferrate: hydrogen resin mixed powder, as an adjunct to pressure, creates a nothing-in/nothing-out seal in well-known ways with blood.

a. The external semi- or non-occlusive vertical pressure is critical to achieving hemostasis. Without pressure, hemostasis is not consistently achieved.

b. Range of the physical factors includes particle size, density, hardness, thickness, shape, dryness, and ingredient proportions.

2. When the preferred 1:7 ferrate: hydrogen resin mixed powder is compressed to at least about 8K psi, a dense solid device is formed. The dense solid device, preferably as a tablet, is able to withstand significant manual pressure and such pressure provides a very strong and uniform force to bear on the wound surface. On the contrary, the same pressure is not easily directed on the loose powder which is scattered unevenly and is relatively thin across the wound bed. Some areas have thicker powder coverage than others and still others with possibly no coverage at all. The nonuniform coverage of the loose powder on the wound site results in lower net pressure than the uniform and higher net pressure achievable through the use of a tablet. In addition, the uniform surface of the solid tablet more evenly displaces blood therebeneath, creating a more uniform seal, and reducing the chance of pooling of blood that may occur with an uneven loose powder application. Consequently, the tablet adheres faster to the bleeding wound and hemostasis is achieved earlier compared to the powder.

3. As a seal is formed from the interaction of blood with the surface of the tablet in contact with the wound, the seal remains intact, protecting the wound, and dissociates itself easily from the rest of the unused solid hemostatic material. If this unused remainder is left attached, a large reservoir of hemostatic material provides persistent long term capacity to arrest further bleeding and promote antimicrobial protection and eventual healing. The extent of the persistent long term action can be designed by the size, shape, density, particle sizes, and thickness of the tablet.

4. The solid hemostatic device can be made to apply on all conceivable surfaces, including horizontal, vertical and angled surfaces.

5. The solid may be compression formed in different shapes or machined into different shapes after tablet formation. Machining may be performed with blades or lasers and may be used to score larger tablets to allow them to be broken into smaller shaped for application.

6. The solid may be a extruded or a continuous ribbon of solid material as any form of mechanical compression may be used.

7. The solid may be attached to adhesive bandages, swabs, surgical or dental instruments, vacuum devices and magnets, if the proper materials such as magnetite are mixed with the powder. The tools attached to the solid hemostat may be straight or bent, rigid or flexible.

8. The solid hemostat may be a single uniform powder compressed into a tablet, or the powders may be layered.

9. Microbial agents maybe added to the powder as a dry powder, absorbed into the resin, or added after the tablet is formed.

10. The solid may be adhered to compression assisting devices such as balloons, compressed foams, mechanical clamps, and compression bandages.

11. Additives such as fibrous material may be used to increase strength of the table, allowing it to be made thinner, flexible, moldable during application, or to improve cosmetic appearance.

12. The tablet may be adhered to a backing which may contain a microbial agent, an adhesive to hold the tablet in place protection of the tablet, or as a cosmetic function.

13. The tablet may be applied to a bleeding wound after a previous treatment.

The following embodiments and aspects thereof are described and illustrated in conjunction with systems, tools and methods which are meant to be exemplary and illustrative and not limiting in scope. In various embodiments one or more of the above-described problems have been reduced or eliminated while other embodiments are directed to other improvements. In addition to the exemplary aspects and embodiments described above, further aspects and embodiments will become apparent by reference to the drawings and by study of the following descriptions.

BRIEF DESCRIPTION OF THE SEVERAL VIEWS OF THE DRAWING(S)

FIGS. 25 to 27C are perspective views of other configurations of one or multiple-piece embodiments affixed to an adhesive bandage.

FIGS. 28 to 33A are perspective views of other configurations of solid one-piece embodiments affixed to a delivery member.

FIG. 34 is a perspective view of another one-piece embodiment.

FIG. 35 is a section view in the direction of arrows 35-35 in FIG. 34.

FIG. 36 is a perspective view of another one-piece embodiment.

FIG. 37 is a section view in the direction of arrows 37-37 in FIG. 36.

FIGS. 37A to 37E are section views of alternate embodiments of FIG. 37.

FIG. 46 shows a series of three separate pictorial representations of the percentage of whole beads to fragments thereof required to form the hemostatic device of this disclosure.

FIG. 47 is a pictorial view of the effect of thickness in formulating the hemostatic device of this disclosure.

Figure 1:
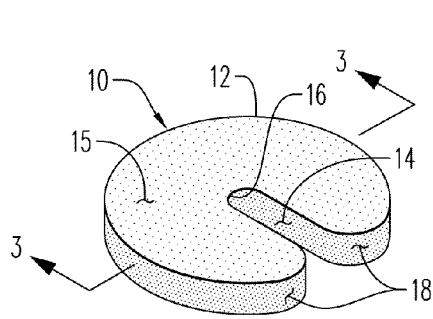
FIG. 1 is a perspective view of a one-piece tablet embodiment of the invention.

Exemplary embodiments are illustrated in reference figures of the drawings. It is intended that the embodiments and figures disclosed herein are to be considered to be illustrative rather than limiting.

DETAILED DESCRIPTION OF THE INVENTION

Nomenclature 10. hemostatic device
11. hemostatic device
12. hemostatic body
13. hemostatic material
14. cannula access slot
15. skin contact surface
16. slot proximal end
17. body segment
18. slot entrance corners
19. cannula access hole
20. hemostatic assembly
21. segment opening
22. foam backing
22a. edge
23. access hole segment
24. rigid backing
25. body segment
26. cannula access slot
30. hemostatic device
32. body halves
34. mating edge
35. skin contact surface
36. catheter access hole halves
37. skin contact surface
38. slot entrance corners
39. foam backing
40. hemostatic device
42. body halves
44. fracture line
45. skin contact surface
46. groove thickness
48. skin contact surface
50. hemostatic device
52. hemostatic body
54. flat skin contact surface
56. convex skin contact surface
58. hemostatic material
60. hemostatic assembly
62. hemostatic body
63. hemostatic material
64. rigid outer backing
66. skin contact surface
68. outer surface
70. hemostatic assembly
72. hemostatic body
73. hemostatic material
74. rigid outer backing
76. skin contact surface
78. outer surface
80, 80', 80". hemostatic bandage
82, 82. adhesive carrier
84, 84". hemostatic body
85. hemostatic material
86, 86'. adhesive surface
88. skin contact surface
90, 90'. hemostatic bandage
92. body array
94. hemostatic body
94'. body array
95, 95'. hemostatic material
96. skin contact surface
97. hemostatic material
98, 98'. skin contact surface
99. tear line
100, 110, 120, 130, 140, 150, 150'. hemostatic device
102, 112, 122, 132, 142, 152, 152'. hemostatic body
104, 114, 124, 134, 154, 154'. handle
106, 116, 126, 136, 146, 156, 156'. skin contact surface
108. flat end surface
118. curvilinear body end
144. flexible cord handle
148. curvilinear body end
158. curvilinear body end
160. hemostatic device
162. hemostatic body
163. hemostatic material
164, 166. convex skin contact surfaces
170. hemostatic device
172. hemostatic body
174. skin contact surface
176. fiber-filled hemostatic material
177. rigid backing
178. foam backing
180. hemostatic body
182. skin contact surface
184. hemostatic material
186. hemostatic body
188. skin contact surface 190. additive hemostatic material
192. hemostatic body
194. skin contact surface
196. hemostatic material
200. array
202. hemostatic body
204. array
206. hemostatic body
210. hemostatic device
212. hemostatic body
214. cannula access hole
216. hemostatic material
220. hemostatic assembly
222. inert carrier
224. adhesive surface
226. irregular hemostatic bodies
230. hemostatic assembly
232. string or wire
234. irregular hemostatic bodies
236. hemostatic mat
240. hemostatic assembly
242. hollow hemostatic body
244. foam insert Broadly, the hemostatic powder composition used to form the hemostatic device of this disclosure, marketed by Biolife, (assignee) under the trademark STATSEAL, preferably includes an effective amount of an insoluble cation exchange material preferably combined with an effective amount of an anhydrous salt ferrate compound. Preferably, the hemostatic powder includes a mixture of the hydrogen form of a cation exchange resin (henceforth notated in short as hydrogen resin) and potassium ferrate. The hemostatic powder can be converted to a tablet by any known compression method into any size, shape, thickness and configuration. Optionally, other materials can be incorporated into the hemostatic powder to enhance performance including: antimicrobial agent, zinc oxide, binders and excipients for aiding tablet formation, magnesium stearate, sodium carboxymethylcellulose, hydroxymethyl cellulose, polyvinylpyrrolidone, medical grade fibers for added strength, natural and synthetic gums.

STATSEAL solid hemostatic devices (also referred to as tablets, discs, and wafers) are intended for use as a topical dressing for bleeding control associated with minor wounds, including control of minor external bleeding and exudates from sutures and/or surgical procedures. STATSEAL devices are preferably composed of two main components: one part potassium ferrate and seven parts hydrophilic polymer, by weight. Potassium ferrate is the oxyacid salt byproduct of the reaction between ferric acid ($H_2FeO_4$) and potassium hydroxide (KOH). Potassium fusion ferrate is manufactured by the thermal combination of iron oxide ($Fe_2O_3$) and potassium nitrate ($KNO_3$). Potassium ferrate readily decomposes in water to produce $Fe_2O_3$ and KOH as follows:

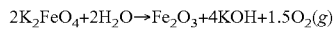

$$2K_2FeO_4 + 2H_2O \rightarrow Fe_2O_3 + 4KOH + 1.5O_2(g)$$

General

The hydrophilic polymer is a strong acid cation ion-exchange resin formed of a sulfonated copolymer of styrene and divinylbenezene (2%) in the hydrogen form. The polymer used in STATSEAL devices (PUROLITE C-122 (H); CAS No., 069011-20-7) is purchased fully hydrated and is simply heat-dried to less than 3% moisture in preparation for combination with the potassium ferrate.

STATSEAL hemostatic devices achieve their principle intended action (hemostasis) by creating a physical barrier or seal to the blood flow. The product establishes an environment in which a natural blood clot can build and form beneath the physical seal formed by STATSEAL. The hemostatic effect of the device is produced by two simultaneous modes of action:

The procoagulating iron-based oxyacid salt coagulates the blood protein.

The hydrophilic polymer rapidly dehydrates the blood and absorbs exudates.

The hydrophilic polymer and oxyacid salt reaction is illustrated below:

$$\text{Resin-H} + K_2FeO_4 \xrightarrow{blood} \text{Resin-K} + Fe_2O_3 + H_2O + O_2$$

As the device contacts blood, the seal begins to form immediately. The polymer quickly absorbs the liquid portion of the blood stacking the blood cells beneath. As the polymer absorbs the liquid it swells. As the cells rapidly stack beneath the tablet, they form the seal. This seal stops bleeding and also prevents further absorption of liquid by the polymer in the tablet. The swollen wetted polymer will allow the portion of the solid hemostat that is in contact with the blood to delaminate from the remaining dry material. The remaining dry tablet may be either removed or held in place with a covering dressing. A small portion of the tablet material remains attached to the surface of the blood or seal. As the wound heals beneath the seal, the remaining material falls off the wound site.

Surprising Results

Because of the reduction in surface area, high density and hardness of the solid hemostatic device, expectations were that a much longer time would be required to achieve hemostasis in a bleeding wound as compared to the free powder. Surprisingly, hemostasis was achieved in a shorter time than in the case of the free powder. Furthermore, the proximal side of the tablet developed adhesion to the bleeding wound site more rapidly than the free powder. The unexpected finding is rationalized as follows. When the solid hemostatic tablet is applied on a bleeding wound, a manual pressure applied on the distal side of the tablet imposes a very strong and uniform force on the wound surface. On the contrary, the same pressure is not easily directed on the bare powder which is scattered unevenly and is relatively thin in some areas across the wound bed, with some areas possibly with no powder coverage, resulting in lower net pressure. Consequently, the tablet adheres faster to the bleeding wound and hemostasis is achieved earlier compared to the free powder.

Another surprising finding with the tablet is the quick separation of the formed seal from the unused portion of the tablet. The seal is formed readily by the interaction of blood with the surface of the tablet in contact with the wound as discussed earlier. The quick separation between the used and unused portion of the tablet is unexpected. The seal remains intact to protect the wound while the tablet separation process is proceeding. This leaves a large reservoir of unreacted solid hemostatic material allowing persistent long term capacity to stanch further bleeding, and provide antimicrobial protection and eventual healing.

The extent of the persistent long term action can be designed by the size, shape and thickness of the tablet. The foregoing examples of size, shape and thicknesses of the tablet and limitations related therewith are intended to be illustrative and not exclusive. Moreover, the hemostatic device can be made to apply on all conceivable surfaces, including horizontal, vertical and angled surfaces. The particle size of the hemostatic powder determines, in part, the integrity of the device, particularly in the absence of a binding agent. The preferred particle size range is 80 microns to 500 microns, more preferably, 150 to 300 microns. Below 80 microns, the seal is too thin and weak while above 500 microns, the seal is not uniform and too thick with weak spots.

Any form of insoluble cation exchange material can be selected as a component of the hemostatic tablet. Preferably the cation exchange material is a cation exchange resin that is crosslinked in the range of 0.25% to 15%. The hydrogen form the cation exchange resin is preferred over other cation forms.

Embodiment Details

Figure 2:
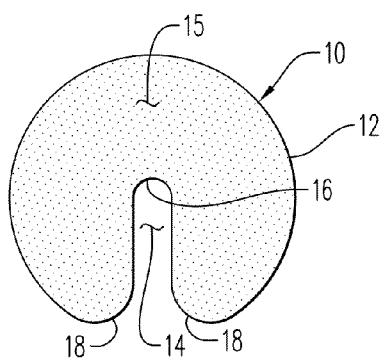
FIG. 2 is a top plan view of FIG. 1.
Figure 3:
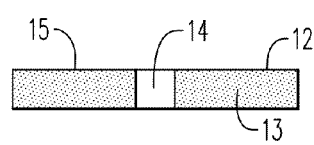
FIG. 3 is a side elevation view of FIG. 2.

Referring now to the drawings, and firstly to FIGS. 1 to 3, one embodiment of the invention is there shown generally at numeral 10 and includes a circular body 12 formed of hemostatic material, the content, physical properties of which will be described herebelow. The body 12, sometimes referred to as a wafer body, a disc, or a tablet, includes an elongated cannula access slot 14 formed radially inwardly from the perimeter to the center of the body 12, terminating at a slot proximal end 16. To facilitate installation around an I.V. cannula as shown in FIGS. 7 and 8, radiused slot entrance corner 18 forming the inlet end of the cannula access slot 14 are provided.

Figure 7:
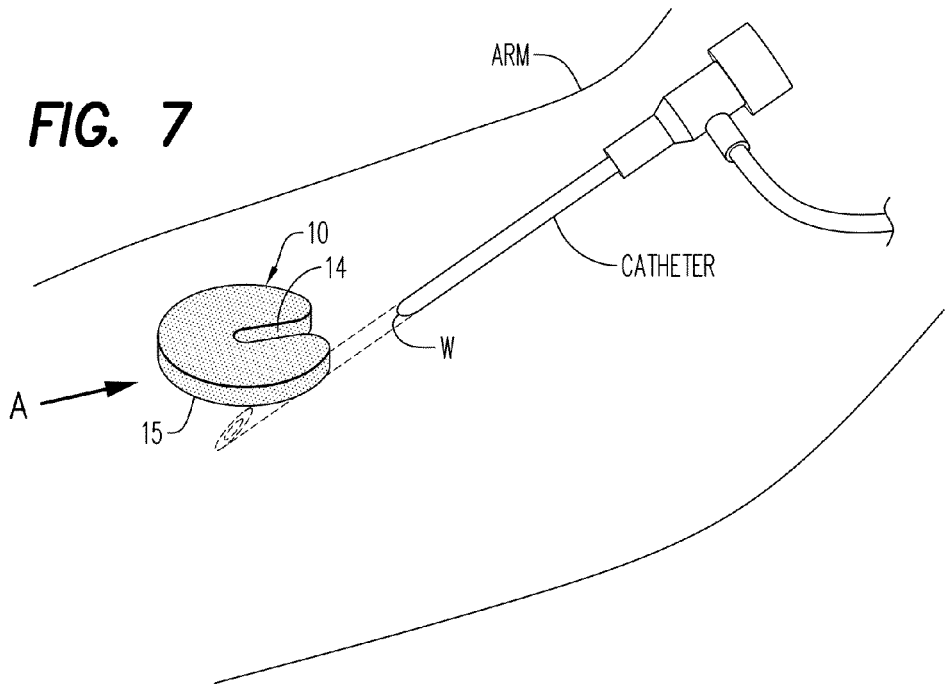
FIGS. 7 to 10 are perspective views showing the deployment of the embodiment of FIG. 1 onto a patient's arm as an I.V. catheter is being removed.
Figure 8:
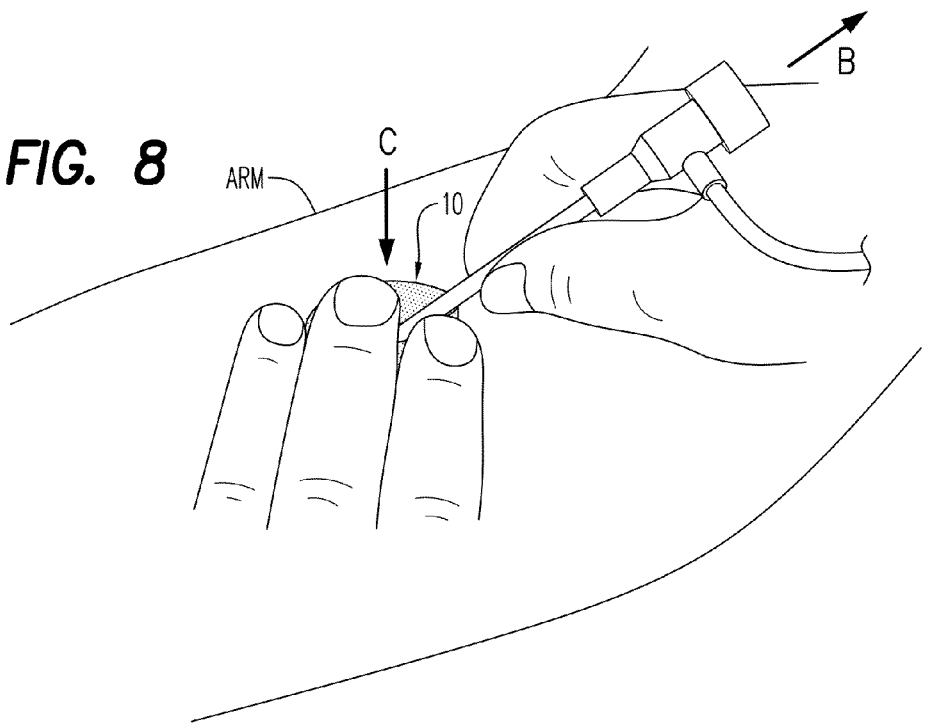
Figure 9:
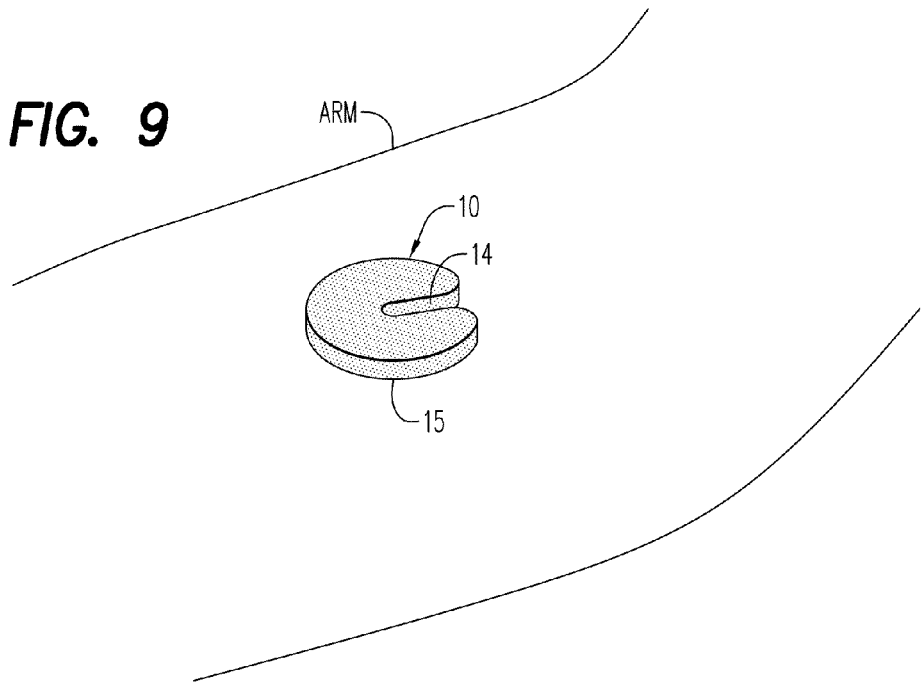
Figure 10:
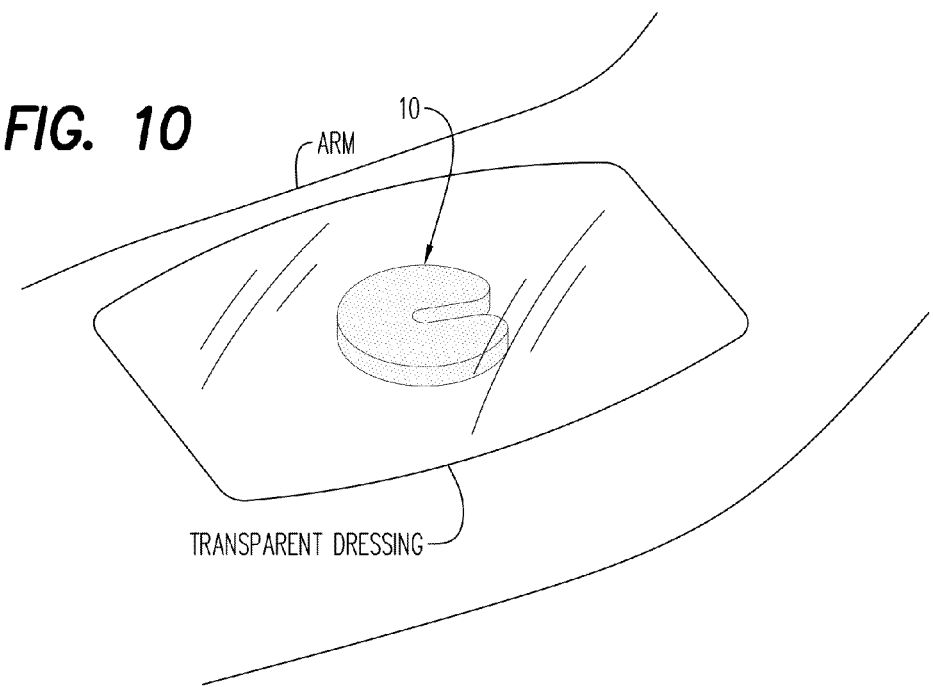

As seen in FIG. 7, the hemostatic device 10 is positionable in the direction of arrow A so that the catheter, needle or cannula access slot 14 slides around the catheter and is positioned against the skin of the arm at the wound site W. The skin contact surface 15 of the hemostatic device 10 is then pressed against the skin in the direction of arrow C in FIG. 8 for a time sufficient for the hemostatic material of the device 10 to interact with blood and exudate from the wound site W, after which the catheter is removed in the direction of arrow B. With the hemostatic device 10 in the position shown against the skin of the arm in FIG. 9, a transparent dressing is applied thereover to protectively cover and hold the hemostatic device 10 in position over the wound site.

Figure 3A:
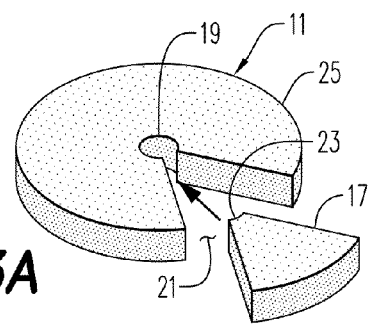
FIG. 3A is a perspective view of a two-piece tablet embodiment of the invention.

Referring now to FIG. 3A, an alternate embodiment of the hemostatic device is there shown at numeral 11 and includes a body segment 25 having a central cannula access hole 19 formed therethrough. The body segment 25 includes a segment opening 21 into which a wedge-shaped body 17 may be inserted in the direction of the arrow after the cannula has been placed through the slot access cannula access hole 19. An access hole segment 23 completes the cannula access hole 19 surrounding the cannula when it is properly installed.

Figure 4:
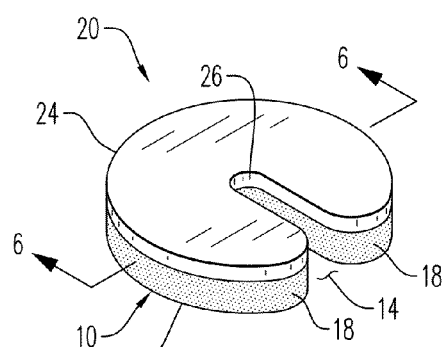
FIG. 4 is a perspective view of an alternate embodiment of FIG. 1 showing the addition of a reinforcing foam backing.
Figure 5:
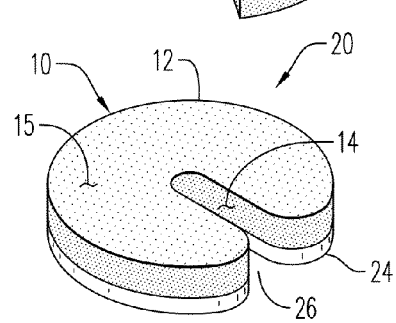
FIG. 5 is a reverse perspective view of FIG. 4.
Figure 6:
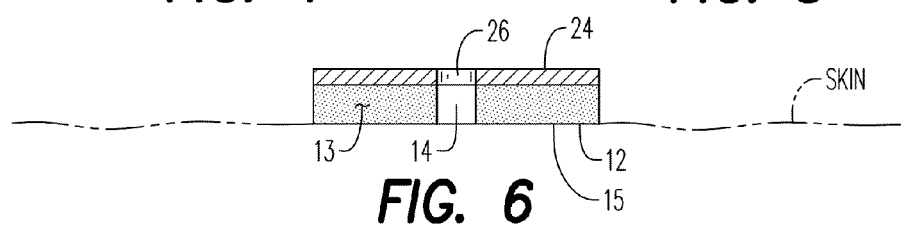
FIG. 6 is a section view in the direction of arrows 6-6 in FIG. 4.

Referring now to FIGS. 4 to 6, another embodiment of the invention is there shown at numeral 20 and includes the hemostatic device 10 of FIG. 1 adhesively attached to a matingly shaped layer of rigid backing 24 which covers one surface of the body 12. The proximal surface of the body 12 defines the skin contact surface 15.

Figure 6A:
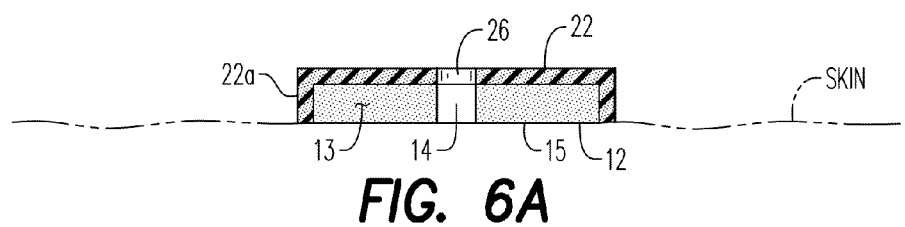
FIG. 6A shows an alternate embodiment of FIG. 6.

Yet another embodiment of the invention is shown at FIG. 6A which includes the previously described hemostatic device 10 formed of a body 12, the body 12 being comprised of compressed together hemostatic material 13 as described herebelow. Foam backing 22 is provided and includes edges 22a which completely surround the otherwise exposed perimeter edges of body 12, but do not cover the skin contact surface 15.

Figure 11:
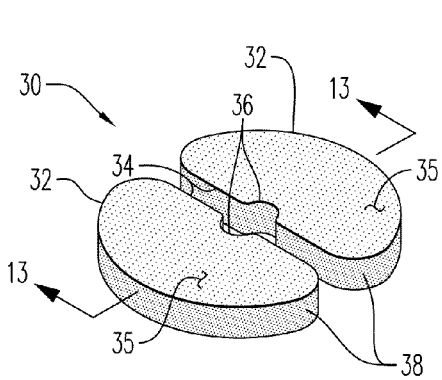
FIG. 11 is a perspective view of another two-piece embodiment.
Figure 12:
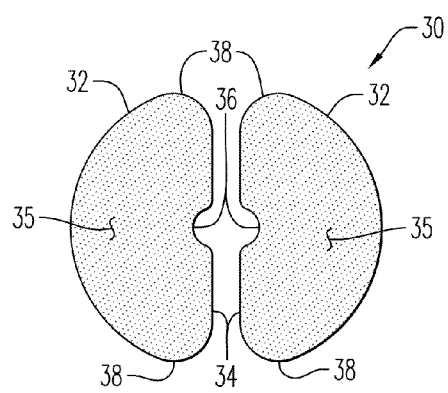
FIG. 12 is a top plan view of FIG. 11.
Figure 13:
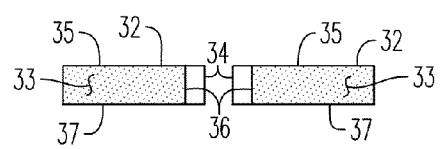
FIG. 13 is a section view of arrows 13-13 in FIG. 11.

A preferred embodiment of the invention is shown generally at numeral 30 in FIGS. 11 to 13 formed of hemostatic body halves 32 which are mateable together along proximal mating edges 34. Centrally positioned catheter access hole halves 36 are formed into the proximal edges 34 to surround the catheter when the skin contact surfaces 35 or 37 are positioned therearound against the skin. Rounded corners 38 are provided to reduce body breakage. The preferred dimensions of each of the halves 32 of this embodiment 30 are: l=0.82"; w=0.44"; t=0.13", slot diameter=0.12".

Figure 13A:
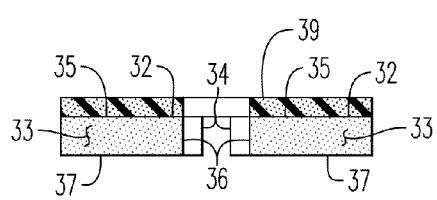
FIG. 13A is a section view similar to FIG. 13 showing the addition of a reinforcing foam backing.

Referring to FIG. 13A, another embodiment of the invention which includes the hemostatic device 30 of FIG. 11, also includes a strengthening foam backing 39 adhesively attached to one surface 35 of each of the body halves 32, the skin contact surface 37 remaining free for skin attachment during installation.

Figure 14:
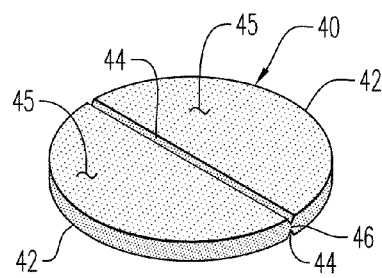
FIGS. 14 and 15 are perspective views of other one-piece tablet embodiments.

In FIG. 14, another embodiment of the hemostatic device is there shown at 40 and includes body halves 42 which are connected along fracture line 44 and held together by a groove thickness 46 of hemostatic material. The purpose of this embodiment 40 is to facilitate fracture of the body halves 42 along the fracture line 44 to be easily broken to accommodate better skin surface contact in an area of curved skin surfaces.

Figure 15:
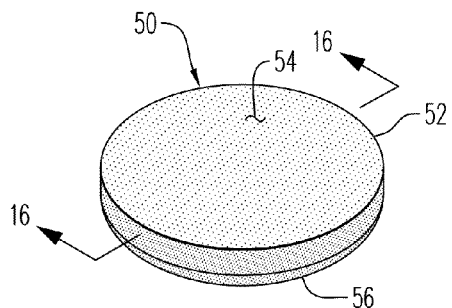
Figure 16:
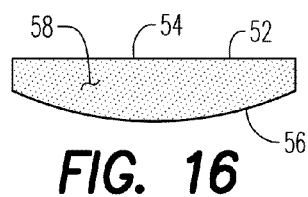
FIG. 16 is a section view in the direction of arrows 16-16 in FIG. 15.
Figure 17:
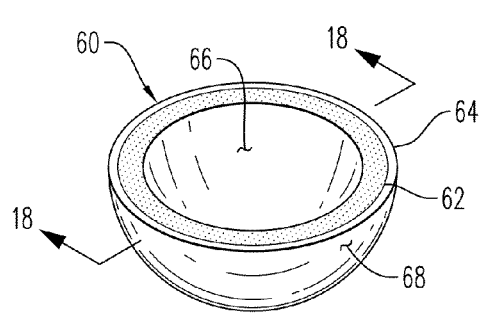
FIGS. 17 to 24 are perspective and corresponding section views of hollow specialty configurations of the invention.
Figure 19:
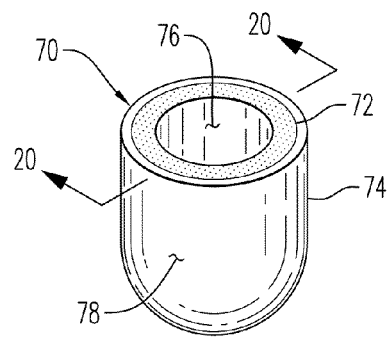
Figure 18:
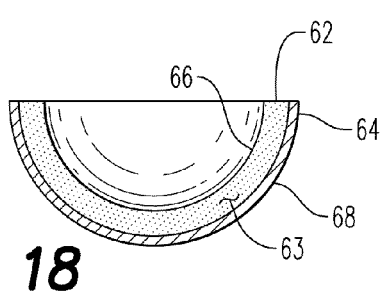
Figure 20:
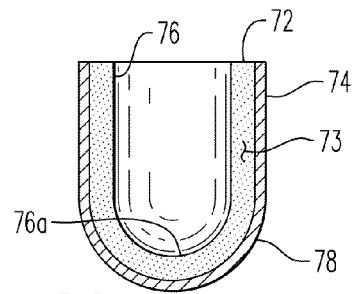
Figure 21:
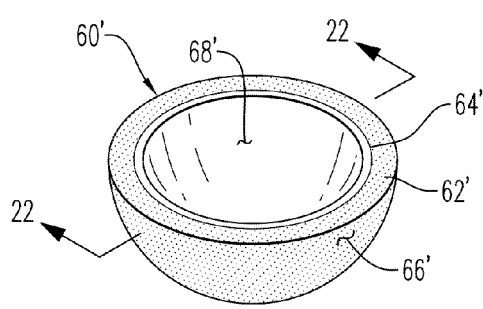
Figure 23:
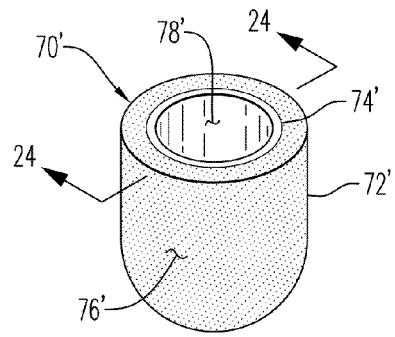
Figure 22:
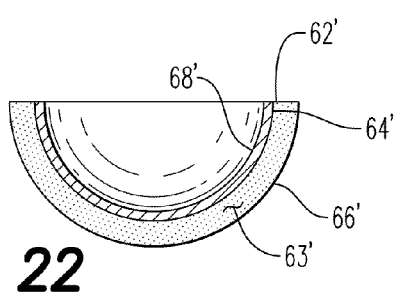
Figure 24:
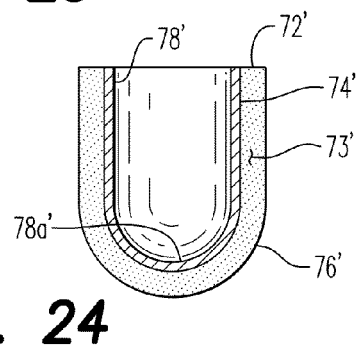

In FIGS. 15 and 16, the hemostatic device 50 formed of a body 52 having a flat skin contact surface 52 and a convex skin contact surface 56 is provided.

Referring now to FIGS. 17 to 24, a series of hollow specialty configurations of the invention are there shown. Each of these hemostatic assemblies 60 and 70 provide a concave curvilinear skin contact surface 66 and 76, respectively, formed of a cup or thimble-shaped hemostatic body 62 and 72, respectively. To add strength to each of these hemostatic assemblies 60 and 70, a rigid or semi-rigid outer backing 64 and 74, respectively, having a smooth protective outer surface 68 and 78, respectively, are provided. A particular use embodiment may be for a bleeding fingertip or toenail of a dog when trimmed too short.

Then, in FIGS. 21 to 24, convex or spherically-shaped outer skin contact surface 66' and 76' of cup or thimble-shaped hemostatic bodies 60' and 70', respectively, are provided. These hemostatic bodies 62' and 72' are supported on their inner surfaces by adhesive attachment to a rigid or semi-rigid mating outer backing 64' or 74', respectively. Referring now to FIGS. 25 to 27C, a series of hemostatic bandages 80, 80', 90, and 90' are there shown. Each of these hemostatic bandages include an elongated strip of flexible adhesive carrier 82 having an adhesive surface 86 thereon. In embodiment 80, a circular tablet-shaped body 84 formed of hemostatic material 85 and having a skin contact surface 88 is centrally positioned and adhesively attached to the adhesive carrier 82. The hemostatic bandage 90 includes a rectangular-shaped body 94 formed of compressed together hemostatic material 95 as described herebelow and also having a skin contact surface 98.

With respect to the hemostatic bandage 90' in FIG. 27A, an array 94' of thin, smaller hemostatic bodies are attached to the adhesive surface 86, each of which are formed of hemostatic material 95' and having a skin contact surface 98'. This embodiment 90' provides for flexibility of the skin contact surfaces 98' over an irregularly or curve-shaped skin surface. Likewise, the embodiment 80' in FIG. 27B includes a body array 92 of thin, small hexagonally-shaped hemostatic bodies, each of which is formed of hemostatic material 97 and having a skin contact surface 96. This body array 92 provides alternative ability to conform to curved and irregular skin surfaces.

In FIG. 27C, embodiment 80" provides the adhesive carrier 82" having spaced transverse tear or cut lines 98 to easily adjust the length of the adhesive carrier 82'. A row of very small closely spaced hemostatic bodies 84', adhesively attached to adhesive surface 86' and extending lengthwise along the flexible adhesive carrier 82', are alignable over an elongated wound, for example, a sutured wound. The individual hemostatic bodies provide great flexible adaptability over a contoured skin surface.

Referring to FIGS. 28 to 33A, an array of a plurality of hemostatic devices 100, 110, 120, 130, 140, 150 and 150' are there shown, each having a solid uniquely configured hemostatic body 102, 112, 122, 132, 142, 152 and 152' providing skin contact surfaces 106, 116, 126, 136, 146, 156 and 156' attached to an elongated handle 104, 114, 124, 134, 144, 154 and 154'. Each of the configurations of the solid hemostatic bodies may be adapted to deal with bleeding wounds at various body sites. The flexible cord handle 144 of embodiment 140 provides an additional adaptation for replacement and withdrawal of the hemostatic body 142, while the curved handle 154' facilitates manipulation and positioning of the contoured irregular hemostatic body 152'.

Referring now to FIGS. 34 and 35, still another hemostatic device 160 is there shown formed of a body 162 having outwardly extending curvilinear skin contact surfaces 164 and 166. These surfaces 164 and 166 may be identical or may be of differing curvature to enhance versatility in the application of this embodiment 160. The body 162 is formed of hemostatic material 163 as described herebelow.

Referring now to FIGS. 36 and 37, another one-piece embodiment of the invention is there shown generally at numeral 170 having reinforcing fibers blended with the hemostatic material 176 prior to the body 172 being pressure formed. Opposing skin contact surfaces 174 are provided. Then, in FIG. 37A, the reinforced hemostatic material 176 of body 172 is further reinforced by a screen backing 177 adhesively attached to one of the skin contact surfaces 174. In FIG. 37B, the body 172 is reinforced by a thicker reinforcing foam backing 178, while in FIG. 37C, the body 180 is formed having a mesh material blended with the hemostatic material 184. In FIG. 37D, a very open foam filled rigid or semi-rigid hemostatic powder 190 is utilized to form the hemostatic body 186. Lastly, in FIG. 37E, various additives may be blended with the hemostatic material 196 to form the hemostatic body 192 having skin contact surfaces 194. Note that the additives 196 blended with the hemostatic material may be in various forms, including binding additives, lubricants and antimicrobials.

Figure 38A:
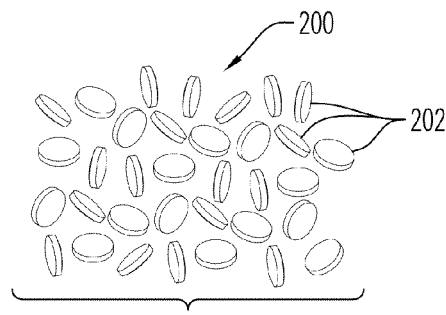
FIGS. 38A and 38B are top plan views of smaller pellets of the invention.
Figure 38B:
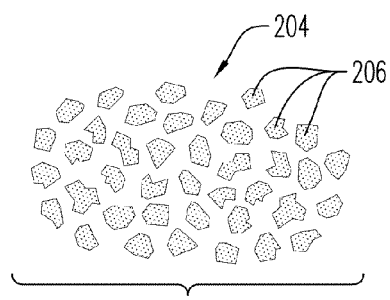

In FIGS. 38A and 38B, arrays 200 and 204 of miniature solid hemostatic bodies 202 and 206 are provided which are compression formed of the powderous hydrostatic material, but, although smaller in size, nonetheless reduce the mess associated with the loose granular hydrostatic powder material. Hemostatic bodies 202 and 206 may be in a form and size similar to KITTY LITTER which, again, reduce the messiness associated with the powderous hemostatic material used to press form these hemostatic bodies 202 and 206.

Figure 39:
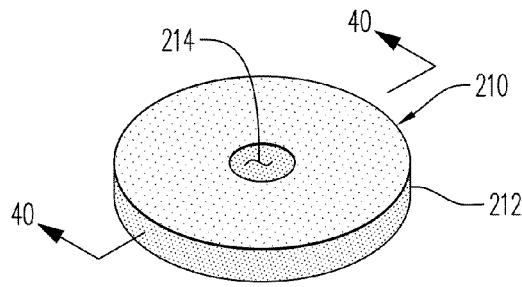
FIG. 39 is a perspective view of another one-piece tablet embodiment.
Figure 40:
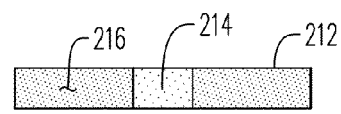
FIG. 40 is a section view in the direction of arrows 40-40 in FIG. 5.
Figure 41:
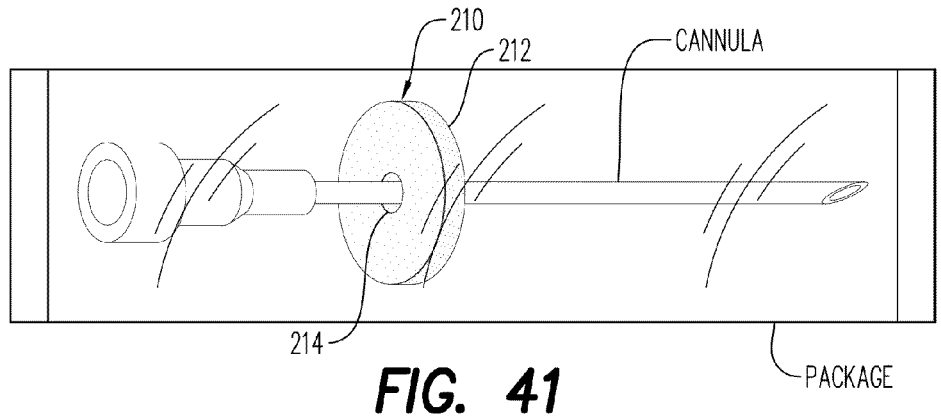
FIG. 41 is a perspective view of the embodiment of FIG. 39 packaged with an I.V. cannula inserted through the central aperture.

Referring now to FIGS. 39, 40 and 41, a completely circular tablet-shaped hemostatic device 210 formed of an annular-shaped hemostatic body 212 is there provided. A central hole 214 is formed there through sized to receive the cannula of a catheter slidably inserted therethrough and which may be packaged as shown in FIG. 41 ready for use.

Figure 42:
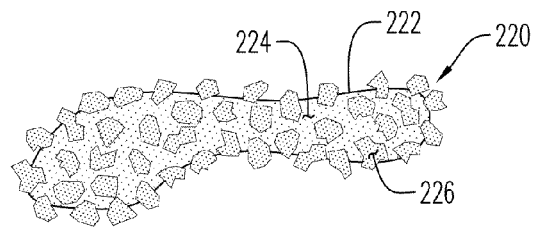
FIG. 42 is a perspective view of the granules of FIG. 38B stuck to the surface of a pliable wax-like shape for odd-shaped wounds.
Figure 43:
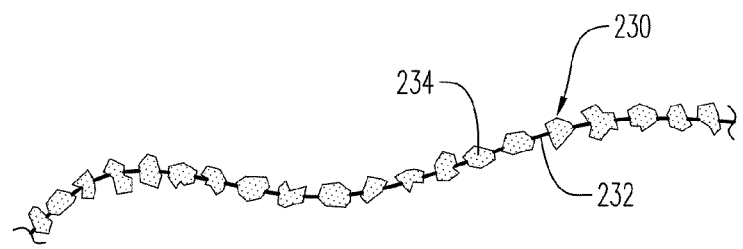
FIG. 43 is a perspective view of the granules of FIG. 38B attached to a length of cord, string or rope.
Figure 43A:
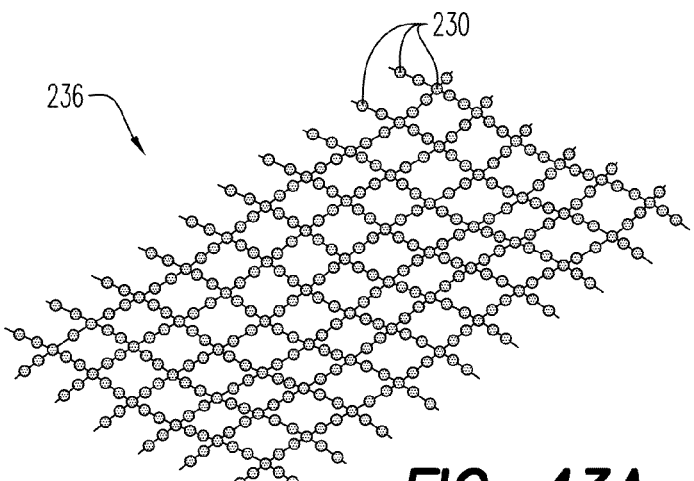
FIG. 43A shows a plurality of the hemostatic assemblies 230 of FIG. 43 woven together to form a hemostatic mat 236.

In FIG. 42, a plurality of small solid hemostatic irregular bodies 226 are attached to a pliable, resilient inert carrier 222 having an adhesive surface 224 to form the hemostatic assembly 220 there shown. This embodiment 220 facilitates applying pressure of the hemostatic bodies 226 against various irregular skin surfaces. FIG. 43 shows an embodiment 230 of irregular hemostatic bodies 234 which have been strung along the length of a string or wire 232. Then, in FIG. 43A, a plurality of these hemostatic assemblies 230 may be woven together to form a hemostatic mat 236.

Figure 44:
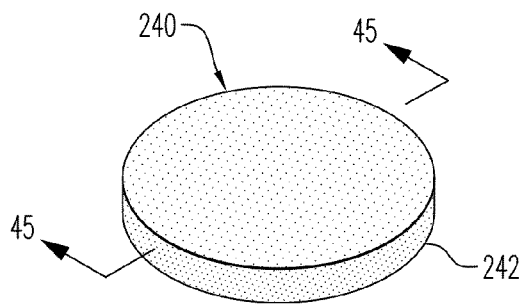
FIG. 44 is a perspective view of a hollow wafer embodiment encasing a foam inner core.
Figure 45:
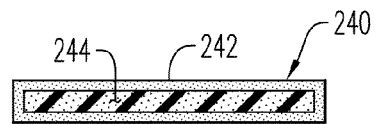
FIG. 45 is a section view in the direction of arrows 45-45 in FIG. 44.

In FIGS. 44 and 45, to reduce the volume of compressed hemostatic material, a hollow hemostatic body 242 encasing a foam insert 244 form the hemostatic assembly 240.

EXAMPLE 1

Formation Pressure

The hemostatic composition for the powder is preferably 1:7 weight mixture of ferrate: hydrogen resin, although this ratio has a range of 1:3 to 1:12. The hydrogen resin is, preferably, the hydrogen form of the 2% crosslinked, sulfonated poly(styrene) resin. The hydrogen resin is available in whole insoluble beads in the range of 500 microns or can be ground into much finer fragments averaging in size from 80 microns to 200 microns. Device formation is based, in part, on the percent of resin fractured to whole beads. The crosslinked hydrogen ion exchange resin will not melt as temperature is increased nor will it cold flow with pressure. Therefore whole resin beads alone cannot be formed into a tablet with pressure.

As seen in FIG. 46, column 3, at 45 k psi, whole beads will not bind together into a solid. As shown in column 3 in FIG. 46, mixtures of whole beads and fragments (61 to 89%:39 to 11%) will bind together. A sufficient percentage of fragments to whole beads (40 to 100%:0 to 60%) as shown in column 1 are required to form a usable solid by filling voids created by stacking the whole beads to allow sufficient interaction for mechanically binding the material together into a tablet.

All or some portion of the fragments may be resin alone or may be replaced with other additives to fill the voids between the whole resin beads. Those additives may be one or a combination of: potassium ferrate (preferred), binders (stearates, waxes), solid lubricants, microbial agents, other amorphous solid materials (calcium carbonate), other non-spherical absorbent materials that are dissimilar in size to the resin, to increase the packing density and contact surfaces to allow a strong tablet to be formed.

EXAMPLE 2

Minimum Thickness

As seen in FIG. 47, the hemostatic powder preferably of 1:7 potassium ferrate: hydrogen resin, was made into solid bodies in tablet form using a lab press. Preliminary tablet formation testing of tablet thicknesses from about 0.5 mm to 30 mm established a minimum thickness of about 0.5 mm for compressing the hemostatic powder into a solid device. The photos in FIG. 47 indicate that at least 0.5 mm thickness is needed to create a complete usable tablet. The material was ground to <250 µm. However, changing the grind size may affect the minimum thickness of powder needed to create a complete tablet. Based on handling or usability, the thin (0.53 mm) 20 mm diameter tablet created with 45K psi (#3) had more integrity than did the thin tablet at 29K psi formation pressure. In Test #1, 29K psi was not sufficient to form a 0.426 mm thick tablet, but in Test #2, a fragile and unstable tablet having a thickness of 0.535 mm was formed.

Three tests were used for the evaluation of a usable hemostatic device for application: Density Test, Formation Test, and Friability Test.

EXAMPLE 3

Density Test

Figure 48:
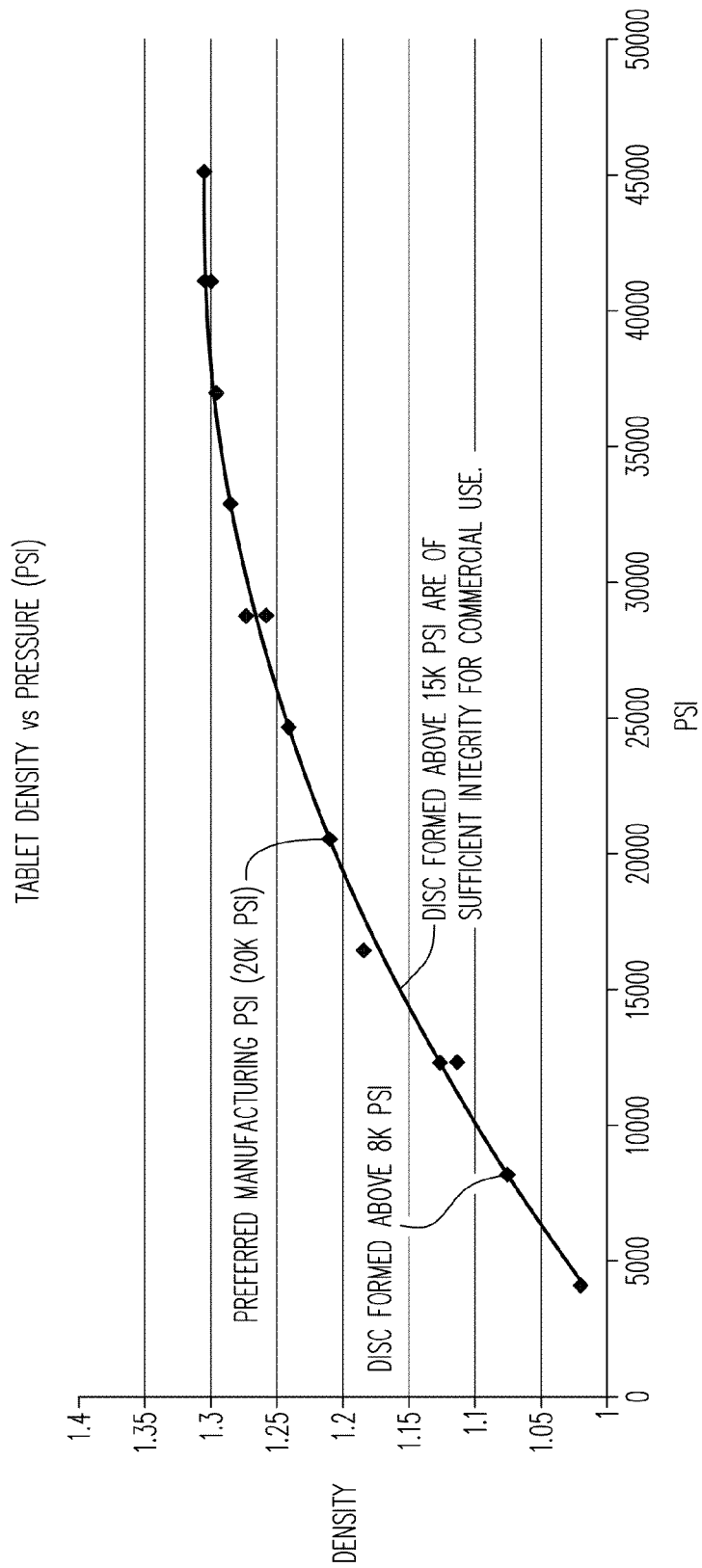
FIG. 48 is a graphic display of hemostatic material density versus formation pressure.

In FIG. 48, a Tablet Density Test was used to determine the relationship of solid density (ml/g) to formation pressure (psi), from 8K to 45K psi. Above 45K psi, the density increase appears to flatten with respect to press pressure. The pressure of 45K psi is the maximum pressure rating for the 20 mm round table die used for testing, to determine the amount of force needed to form a solid tablet. The tablet integrity was determined by measuring harness and wetting rate. In addition, manual breakage of multiple tablets was also used in selecting the appropriate tablet parameters.

Tests on the lab press, a single LANE STOKES disc press, using a ⅛" thick 20 mm round die (0.487 in$^2$) showed that:
- below 8K psi the tablets are too fragile to handle and often break while being removed from the die;
- between 12K and 15K psi, the tablets could be handled but break easily;
- at between 20 L and 33K psi, the tablets are acceptable; further evaluation was performed at 29K psi.

EXAMPLE 4

Friability Test

The Tablet Friability Test is based on the following FDA Guidance for tablets:
Q4B Evaluation and Recommendation of Pharmacopoeial Texts for Use in the ICH Regions: Annex 9 Disc Friability General Chapter
http://www.fda.gov/downloads/Drugs/GuidanceCompliance RequlatoryInformation/Guidances/
UCM176888.pdf Friability is a determination of mass loss during a tumbling test. A tablet is dropped 100 times from a specific height and measurement is taken to determine how much mass is lost. The mean loss should be no more than 1% for tablets, per USP, unless otherwise specified by dosier.

The USP tests ensure that tablets packed in bottle with many other tablets do not lose mass prior to being ingested by the patient. A mass loss would result in a reduction of medication being ingested. In the case of the a topically applied hemostatic tablet there is no prescribed medication and, more importantly the tablets will be packaged as individual units and protected to ensure the tablets are intact on arrival. The risk of any breakage will be mitigated via packaging.

A modified Tablet Friability Test was designed by pouring tablets through a 2" PVC tube from a beaker into a catch beaker. The height from the top of the PVC to the surface of the catch beaker was set at 150 mm (based on the USP Friability Protocol). The Tablet Friability Test showed that the average loss was 2.5%. This amount of loss is acceptable because the tablet is externally/topically applied to the wound surface and, breakage is mitigated through unitized protected packaging.

EXAMPLE 5

Adhesion Test

The 20 mm diameter tablet and the free powder prepared from the same composition consisting of 1:7 potassium ferrate: hydrogen resin, were tested for in terms of their ability to achieve adhesion to the blood surface. A blood seal test was employed as follows:

1. 0.10 mL of EDTA stabilized porcine blood was placed and spread evenly in the one inch diameter circle outlined in a plastic boat;
2. The test material was poured or placed on the top of the evenly spread blood;
3. Moderate manual pressure was placed on top of the test material for 90 seconds;
4. Using a spatula, the blood seal formed by action of blood and the test material was tested for adhesion and strength by scrapping with a spatula.

The results showed that the free powder created an uneven blood seal with moderate adhesion and upon scrapping, provided moderate strength in terms of the lifted seal. The excess portion of the unused free powder had been exposed to and deactivated in the atmosphere and has lost most of its capacity for further use. On the other hand, the 20 mm diameter tablet broke open into two parts, the first part revealed a thicker blood seal with excellent adhesion and strength and, the second part having a significant portion of the tablet unused and intact. The second portion constituting the used tablet remains as a reservoir to stop bleeding and absorption of exudates.

EXAMPLE 6

Hemostasis Comparison Powder Vs. Solid Tablet

Figure 49:
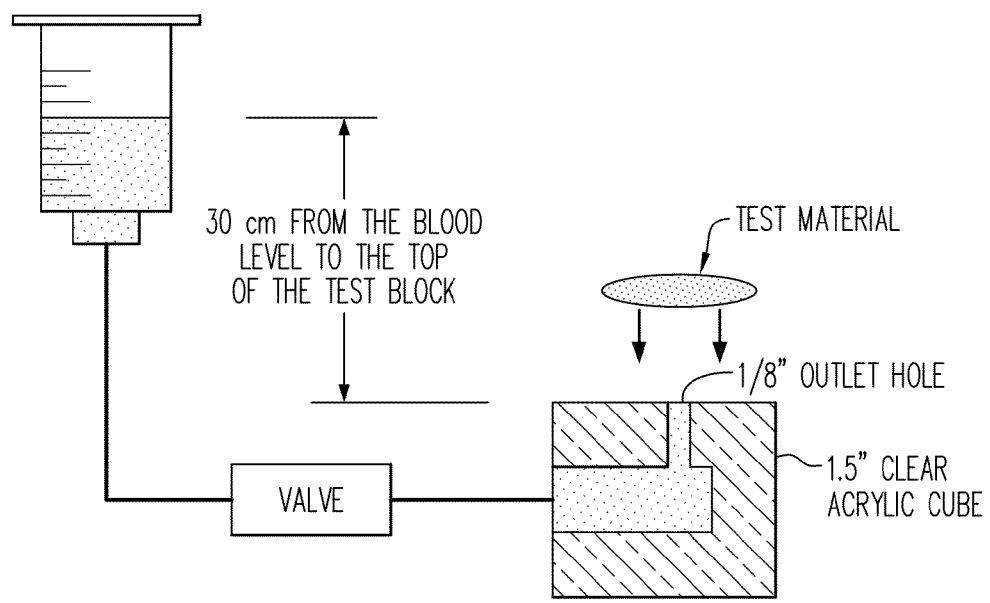
FIG. 49 is a schematic view of a lab test set up to evaluate the ability of the solid hemostatic device versus the powderous form thereof to achieve adhesion to a blood surface.

Referring to FIG. 49, the 20 mm diameter tablet and the free powder prepared from the same composition consisting of 1:7 potassium ferrate: hydrogen resin were tested for hemostasis efficacy using a low pressure gravity flow system. The results showed that for a low pressure gravity flow system, there were no impact on hemostasis efficacy by mechanically compressing the powder versus using the powder itself. In the next example, testing at high pneumatic pressure distinctly demonstrate that the tablet surprisingly outperforms the free powder.

A 60 ml syringe is filled with approximately 25 ml of blood. The test block formed from a 1.5" clear acrylic block. Assuming the entry hole designed to fit a barbed fitting to connect to ¼" flexible vinyl tubing and a ⅛" diameter outlet hole. The syringe is elevated to 30 cm above the top of the test block, creating a pressure of 30 cm water which equated to 20 mm Hg (mercury).

The valve was opened and the blood was allowed to surface. The valve was closed and the blood was spread over an area approximately 0.5" from the outlet. The test material was placed over the blood covering the outlet hole. Contact pressure was held with a 100 gram mass for 60 seconds. After the 60 seconds the 100 gram mass was removed and the valve was opened for 30 seconds. If no blood exits the hole sealing of the hole occurred and the test sample passed the test.

As shown in Table 1 below, both the powder (N=5) and the Tablet (Tablet) (N=10) passed all testing.

TABLE 1

Hemostasis comparison powder to tablet

| | Powder | Solid Tablet |
|---|---|---|
| 1 | Pass | Pass |
| 2 | Pass | Pass |
| 3 | Pass | Pass |
| 4 | Pass | Pass |
| 5 | Pass | Pass |
| 6 | — | Pass |
| 7 | — | Pass |

TABLE 1-continued

Hemostasis comparison powder to tablet

| | Powder | Solid Tablet |
|---|---|---|
| 8 | — | Pass |
| 9 | — | Pass |
| 10 | — | Pass |

EXAMPLE 7

Sealing Test

Powder Vs. Solid Tablet

Figure 50:
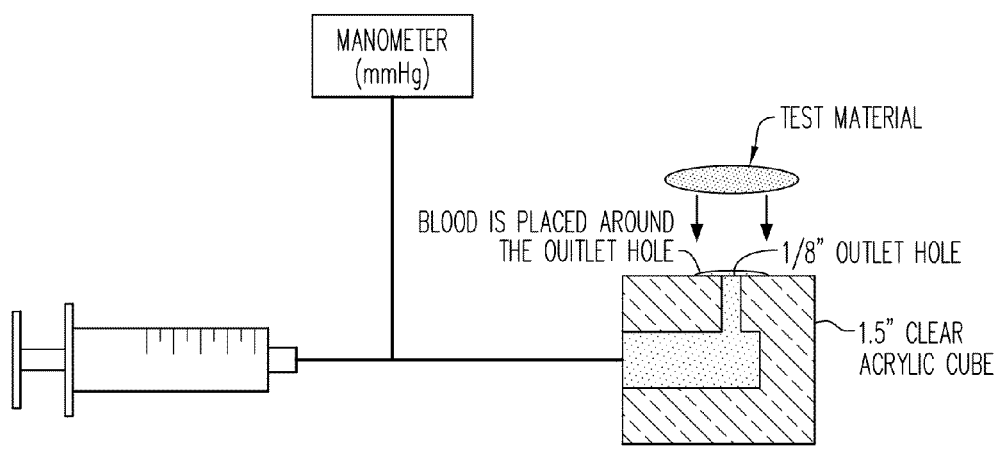
FIG. 50 is a schematic view of an alternate lab test to that shown in FIG. 49 wherein a syringe is utilized to achieve higher static pressure in evaluating the blood adhesion characteristics of a hemostatic tablet versus a free powder hemostatic material.
Figure 51:
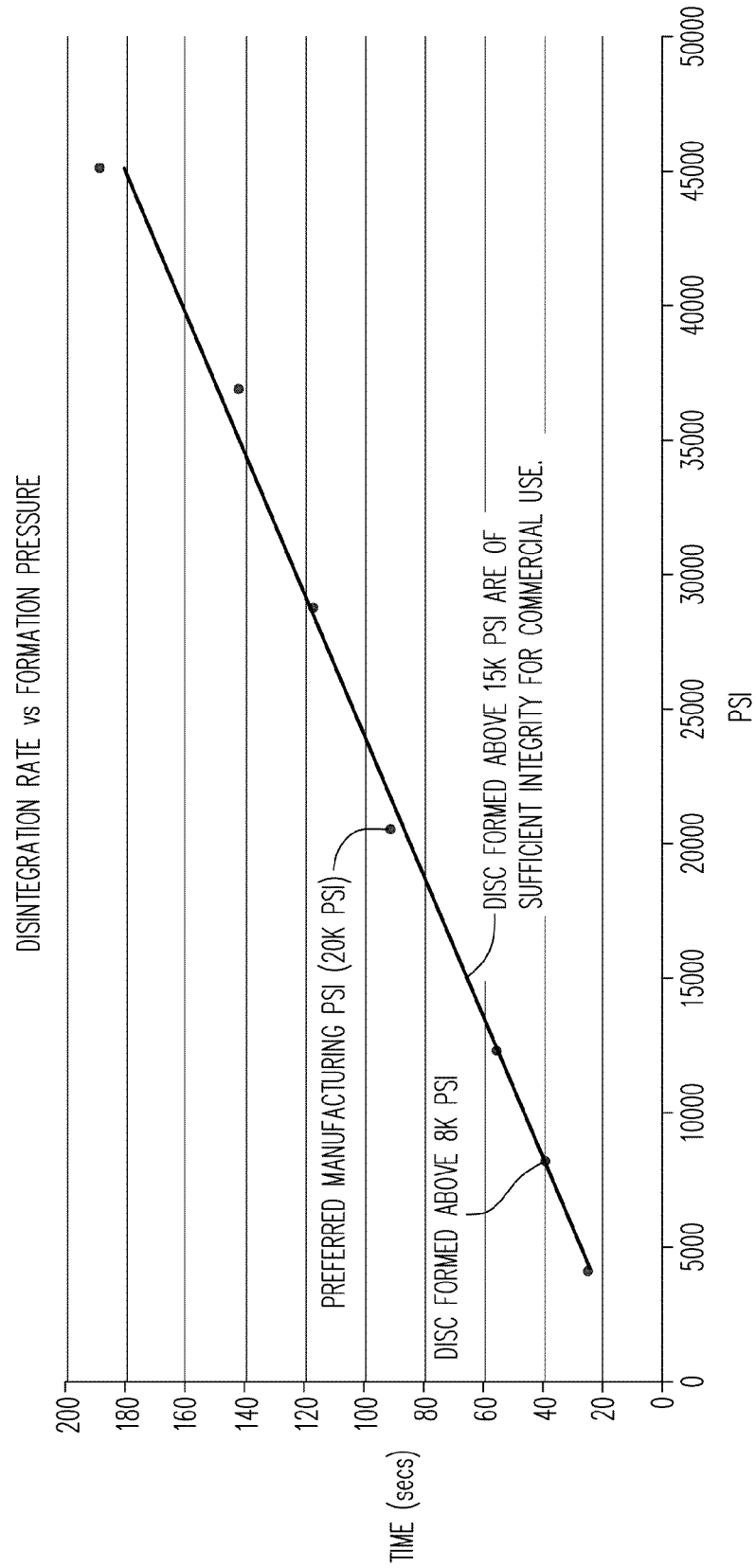
FIG. 51 is a graphic representation of the hemostatic device disintegration rate versus formation pressure.
Figure 52:
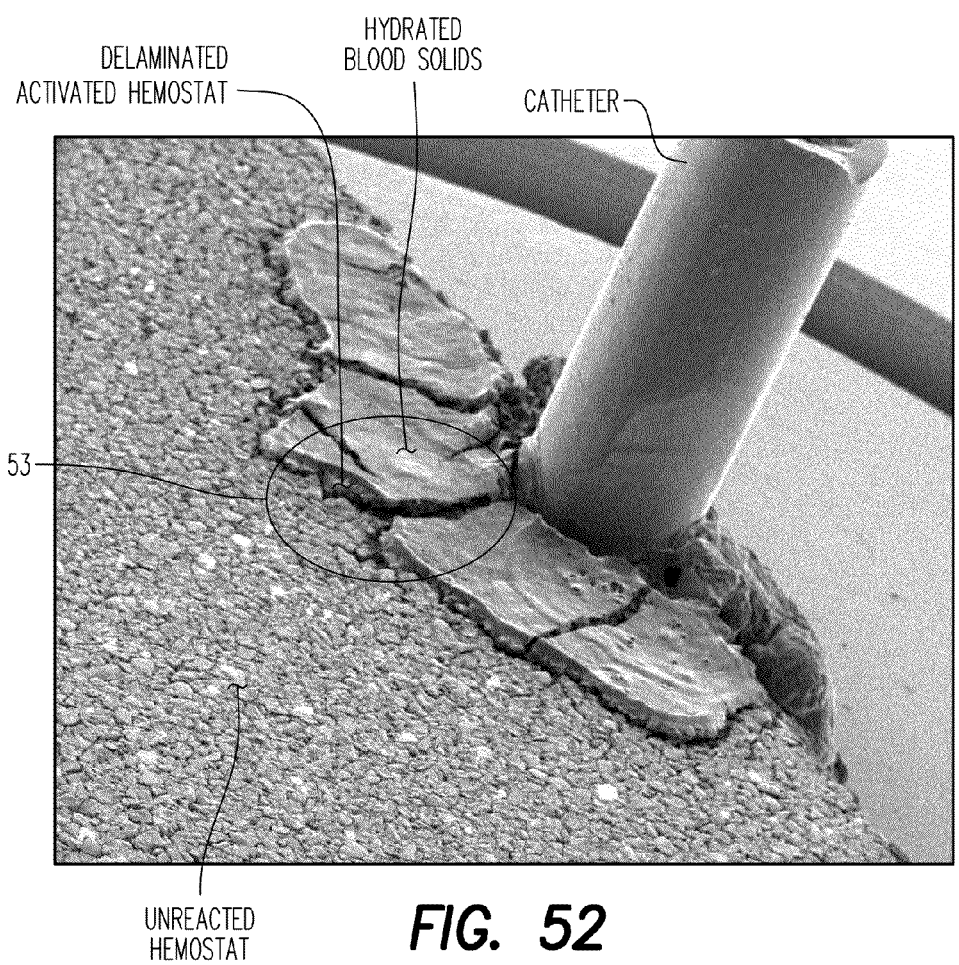
FIG. 52 is a scanning electron microscope (SEM) photo of the hemostatic device of FIG. 11 having been positioned around a vascular accessed cannula.
Figure 53:
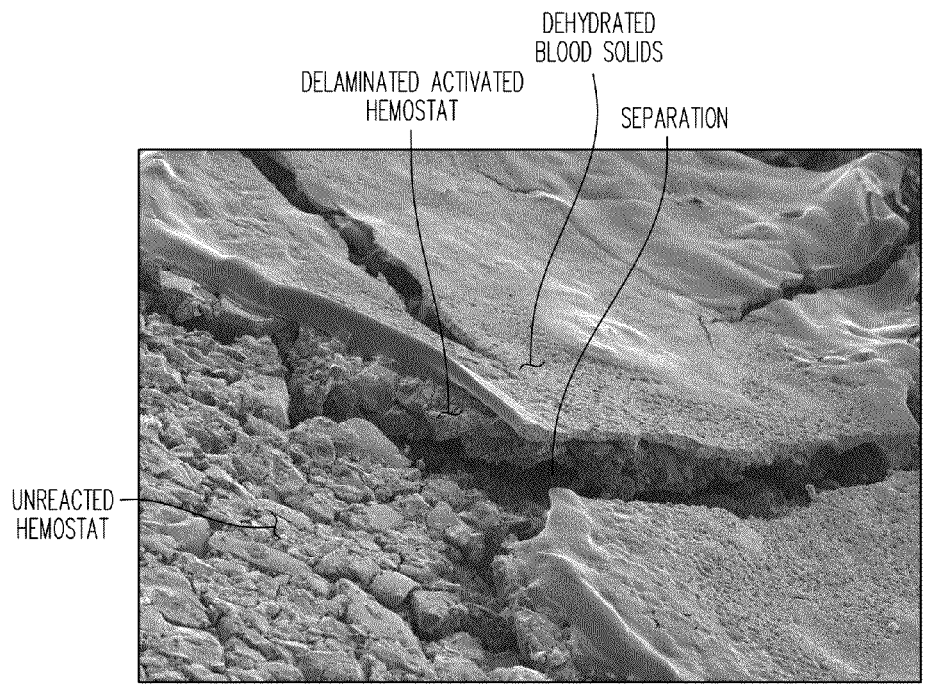
FIG. 53 is an enlarged view of area 53 in FIG. 52.
Figure 54:
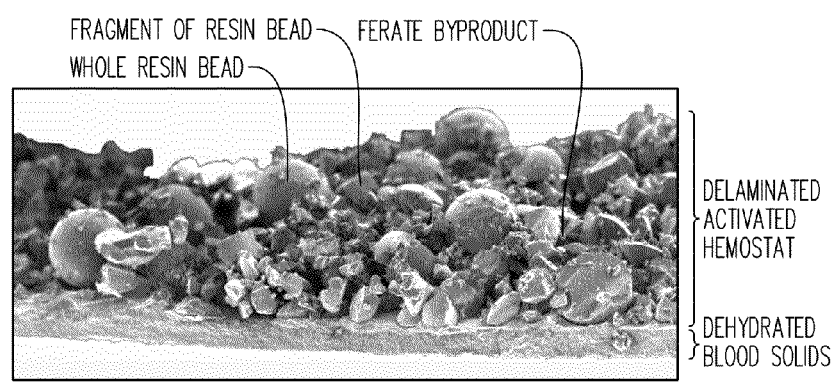
FIG. 54 is a SEM side elevation view of the hemostatic device having been applied atop a bleeding wound.

The 20 mm diameter tablet and the free powder prepared from the same composition consisting of 1:7 potassium ferrate: hydrogen resin, were tested for hemostasis efficacy using a high pneumatic pressure system as detailed below in the study design and experiment. The apparatus is schematically represented in FIG. 50. The results indicated that the tablet was unexpectedly superior to the free powder in hemostasis efficacy during high pneumatic pressure testing. The tablet creates a significantly stronger seal capable of stopping higher pressure bleeding than the free powder that defies expectation. This surprising finding implies that the uniform surface of the tablet enables a much greater manual pressure to be exerted on the blood than the free powder which provides a nonuniform and irreproducible force on the blood. Furthermore, the dense nature of the tablet surface in contact with the blood and the huge reservoir of the composition concentrated in the tablet enable rapid dehydration and significantly better adhesion than for the loose and low density powder. The much greater surface area of the loose powder would lead to the expectation that the powder would perform significantly better than the tablet where less surface is in contact with the blood.

In this test, a test block is created from a 1.5" clear acrylic block. The test block has an entry hole designed to fit a barbed fitting to connect to ¼" flexible vinyl tubing and a ⅛" diameter outlet hole. The first step is to pull back the syringe plunger, power up the manometer and set the manometer to record the maximum value. The syringe plunger is compressed to pressurize the system until the blood seal fails. The manometer records the maximum pressure created just prior to the seal failure. Next blood is placed around the ⅛" outlet hole. The tablet is then placed over the blood. Care is taken to ensure that the blood completely encircles the hole, and that the tablet completely covers the hole as well. A gloved finger is used to apply slight manual pressure to the tablet. The pressure forces the liquid blood from beneath the tablet. The tablet is allowed to set for ~15 seconds and then the plunger is compressed.

During the first attempt, the maximum reading on the manometer reached 408 mm Hg and the tubing dislodged from the syringe. A zip tie was used to prevent future failures, and a pressure of 500 mm Hg was set at an end point.

The tablet was tested 15 times and all consistently reached the end point of 500 mm Hg without failure of the seal. In contrast, the free powder only reached an end point of 100 mm Hg demonstrating the superior and unexpected performance of the tablet.

Comparatively loose powder reached an average hold pressure of 310 mm Hg in the same test. A small foil disk was used to prevent the powder from filling and occluding the hold in the loose powder testing. The powder also required a 75g mass to maintain the seal integrity. Surprisingly the solid preformed better than did the loose powder with no addition mass holding the solid in place above the simulated wound.

EXAMPLE 8

Oxygen Generation

Upon wetting potassium ferrate decomposes. Upon decomposition potassium ferrate released oxygen gas:

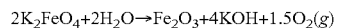

$$2K_2FeO_4 + 2H_2O \rightarrow Fe_2O_3 + 4KOH + 1.5O_2(g)$$

A test is designed to measure the amount of oxygen generated by a mass of PRO OR powder vs. a similar mass of powder compressed into a solid tablet upon wetting. For this test 45K psi was applied to 2-3 grams of powder in a 20 mm diameter tablet die using a lab press. In manufacturing typically 29K psi will be required to produce a 20 mm diameter tablet. This test is using excessive force to further exacerbate any potential for decomposition of potassium ferrate due to mechanical compression of the powder.

This test concluded that upon wetting powder will liberate 3.90 ml of oxygen gas per gram of powder, and powder compressed into a tablet will liberate 4.05 ml of oxygen gas per gram of powder. The percent difference between the oxygen collected in the test for the powder vs. the tablet is 3.77%. This difference is with the 5% coefficient of variance which is used to indicate a good analytical test. Therefore the results are nearly equal and it can be concluded compressing the powder into a tablet does not cause degradation of the potassium ferrate.

In this experiment, a sample of the powder or tablet is placed in a small dry bottle. The bottle is sealed creating a closed system where any gas generated is forced to exit thru a small tube. This outlet of the exit tube is set up to bubble gas into a partially submerged inverted filled graduated cylinder (filled with water). As the gas bubbles into the graduated cylinder it displaces an equal volume of water. This allows for the evolved gas to be measured.

As the powder or tablet is wetted, the potassium ferrate decomposed releasing oxygen. The test material is placed in the dry bottle in the closed system. A syringe is used to inject water into the bottle. In this test, 15 ml of water was injected each time. This volume of water was accounted for in the calculations. Also the graduated cylinder was replaced with a 50 ml burette for more accurate reading of the results. The starting point for the gas measurements was the displacement point created by injecting 15 ml of water into the empty bottle in the closed system.

EXAMPLE 9

Disc Disintegration Test

This test is designed to determine the time for the hemostatic tablet to physically break down into the components in water. The tablet is composed of manually compressed powder composed of a hydrophilic polymer that swells as it absorbs water and potassium ferrate. As the polymer wets and swells it causes disintegration of the tablet. This wetting rate is dependent upon the pressure at which the tablet is pressed.

In this experiment, water is flowed across the tablet in a tube. A screen with approximately 2 mm openings is used to support the tablet in a 2.9 cm diameter tube. A siphon break is elevated to maintain a liquid level 2-3 inches above the screen. The flow rate for the test was 562 ml/min. The end point is when there is no longer any material above the screen.

The pump is turned on. The disc is dropped into the tube with the water running and a stopwatch is started. The disc is observed and, when there is no longer any material above the screen the time recorded.

Nine (9) tablets were produced on a lab press using a 20 mm die and varying amount of force. The machine made sample was produced on a Stokes single lane tablet press. That machine made samples of average weight of 1,500 mg for the Lab Press. Fifteen (15) samples were produced on the Stokes single lane disc press. Average Mass of 750 mg. All tablets tested had a similar thickness of near ⅛".

Disintegration rate is shown to be linear with respect to press pressure for tablets between 8K (disintegration time: 40 seconds) and 45K psi (disintegration time: 180 seconds) for a 20 mm diameter round tablet. Therefore, wetting or disintegration rate is a relationship of the closeness of particles and capillary action to wet the "next" layer of material and minimum preferred disintegration time of 40 seconds is achieved at 8K psi formation pressure.

While a number of exemplary aspects and embodiments have been discussed above, those of skill in the art will recognize certain modifications, permutations and additions and subcombinations thereof. It is therefore intended that the following appended claims and claims hereinafter introduced are interpreted to include all such modifications, permutations, additions and subcombinations that are within their true spirit and scope.

The invention claimed is:

1. A method of arresting the flow of blood from a bleeding wound comprising the steps of:
   providing a hemostatic tablet prepared from a powderous mixture which will hydrate in the presence of blood thereby promoting clotting of the blood;
   said hemostatic tablet defining a proximal portion and a distal portion;
   applying said proximal portion directly to the bleeding wound while a pressure is applied to said distal portion;
   said proximal portion promoting blood clotting at the bleeding wound forming a protective seal over the wound for sealing the bleeding wound;
   said distal portion delaminating from said proximal portion to constitute a reservoir for persistent and long lasting protection against further bleeding and exudation.

2. A method of arresting the flow of blood from a bleeding wound comprising the steps of:
   providing a solid hemostatic tablet defining a proximal portion and a distal portion;
   said hemostatic tablet formed from an insoluble cation exchange material and a salt ferrate;
   applying said proximal portion directly to the bleeding wound in any orientation of the bleeding wound while applying a pressure to said distal portion of said hemostatic tablet;
   promoting blood clotting at the wound with said salt ferrate of said proximal portion;
   forming a protective scab over the wound for sealing the bleeding wound with said cation exchange material of said proximal portion; and
   said insoluble cation exchange material and said salt ferrate of said distal portion delaminating from said proximal portion constituting a reservoir for persistent and long lasting protection against further bleeding and exudation.

3. A hemostatic device adapted to be applied directly to a bleeding wound, comprising: a solid hemostatic tablet defining a proximal portion and a distal portion; a support attached to said tablet to facilitate positioning and holding said tablet against the wound; said proximal portion applied directly to the bleeding wound while a pressure is applied to said distal portion; said proximal portion promoting blood clotting at the bleeding wound forming a protective seal over the wound for sealing the bleeding wound; said distal portion delaminating from said proximal portion to constitute a reservoir for persistent and long lasting protection against further bleeding and exudation.

4. A hemostatic device as set forth in claim 3 wherein: said support is an elongated flexible adhesive carrier having an adhesive surface to which said tablet is attached, said adhesive surface attachable against skin to hold said skin contact surface against the wound.

5. A hemostatic device as set forth in claim 4 wherein: said support is a line having a plurality of closely spaced small said tablets arranged along the length of said line, said line with said tablets capable of being aligned and held by said carrier atop an elongated open or sutured wound.

6. A hemostatic device as set forth in claim 3, wherein: said support is an elongated rigid, semi-rigid or flexible handle attached to said tablet, said tablet being in a regular or irregular three-dimensional form having a uniform or varying cross section.

7. A hemostatic device as set forth in claim 1, wherein: said support includes reinforcing fibers added to, and uniformly blended with, said mixture prior to tablet formation.

8. A hemostatic device as set forth in claim 3, wherein: said support is a three-dimensional pliable, inert carrier having an outer surface onto which a plurality of small said tablets is attached.

9. A hemostatic device adapted to be applied directly to a bleeding wound, comprising: a solid hemostatic tablet defining a proximal portion and a distal portion; a support attached to said tablet to facilitate positioning and holding said tablet against the wound; said hemostatic tablet being formed from an insoluble cation exchange material and a salt ferrate; said proximal portion applied directly to the bleeding wound in any orientation of the bleeding wound when a pressure is applied to said distal portion of said hemostatic tablet; said proximal portion forming a protective scab over the wound for sealing the bleeding wound; and said distal portion delaminating from said proximal portion constituting a reservoir for persistent and long lasting protection against further bleeding and exudation.

10. A hemostatic device as set forth in claim 9 wherein: said support is an elongated flexible adhesive carrier having an adhesive surface to which said tablet is attached, said adhesive surface attachable against skin to hold said skin contact surface against the wound.

11. A hemostatic device as set forth in claim 10 wherein: said support is a line having a plurality of closely spaced small said tablets arranged along the length of said line, said line with said tablets capable of being aligned and held by said carrier atop an elongated open or sutured wound.

12. A hemostatic device as set forth in claim 9, wherein: said support is an elongated rigid, semi-rigid or flexible handle attached to said tablet, said tablet being in a regular or irregular three-dimensional form having a uniform or varying cross section.

13. A hemostatic device as set forth in claim 9, wherein: said support is reinforcing fibers added to, and uniformly blended with, said mixture prior to tablet formation.

14. A hemostatic device as set forth in claim 9, wherein: said support is a three-dimensional pliable, inert carrier having an outer surface onto which a plurality of small said tablets is attached.

15. A hemostatic device for inhibiting bleeding from a catheter wound caused by the presence of the catheter in the wound, comprising: a solid hemostatic tablet defining a proximal portion and a distal portion; a support attached to said tablet to facilitate positioning and holding said tablet against the wound; said hemostatic tablet formed from an insoluble cation exchange material and a salt ferrate; said tablet having two separate half sections which fit together along mating edges to define a catheter access hole for receiving the catheter therethrough; said proximal portion promoting blood clotting at the catheter wound to form a protective scab over the catheter wound for sealing the bleeding of the catheter wound; said distal portion disassociating from said proximal portion constituting a reservoir for persistent and long lasting protection against further bleeding and exudation of the catheter wound.

16. A hemostatic device as set forth in claim 15 wherein: said support is an elongated flexible adhesive carrier having an adhesive surface to which said tablet is attached, said adhesive surface attachable against skin to hold said skin contact surface against the wound.

17. A hemostatic device as set forth in claim 16 wherein: said support is a line having a plurality of closely spaced small said tablets arranged along the length of said line, said line with said tablets capable of being aligned and held by said carrier atop an elongated open or sutured wound.

18. A hemostatic device as set forth in claim 15, wherein: said support is an elongated rigid, semi-rigid or flexible handle attached to said tablet, said tablet being in a regular or irregular three-dimensional form having a uniform or varying cross section.

19. A hemostatic device as set forth in claim 15, wherein: said support is reinforcing fibers added to, and uniformly blended with, said mixture prior to tablet formation.

20. A hemostatic device as set forth in claim 15, wherein: said support is a three-dimensional pliable, inert carrier having an outer surface onto which a plurality of small said tablets is attached.

* * * * *